US009682202B2

(12) United States Patent
Wachtel

(10) Patent No.: US 9,682,202 B2
(45) Date of Patent: Jun. 20, 2017

(54) ADAPTER, INHALATION DEVICE, AND ATOMIZER

(71) Applicant: Boehringer Ingelheim International GmbH, Ingelheim am Rhein (DE)

(72) Inventor: Herbert Wachtel, Ingelheim am Rhein (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/969,293

(22) Filed: Dec. 15, 2015

(65) Prior Publication Data
US 2016/0095992 A1    Apr. 7, 2016

Related U.S. Application Data

(63) Continuation of application No. 13/321,281, filed as application No. PCT/EP2010/002740 on May 5, 2010, now Pat. No. 9,265,910.

(30) Foreign Application Priority Data

May 18, 2009    (EP) ..................................... 09006673

(51) Int. Cl.
*A61M 16/08*    (2006.01)
*A61M 11/06*    (2006.01)
(Continued)

(52) U.S. Cl.
CPC ........ *A61M 15/0086* (2013.01); *A61M 11/00* (2013.01); *A61M 11/007* (2014.02);
(Continued)

(58) Field of Classification Search
CPC ...... A61M 11/00; A61M 11/06; A61M 15/00; A61M 15/0013–15/0016;
(Continued)

(56) References Cited

U.S. PATENT DOCUMENTS

| 1,828,864 A | 10/1931 | Hopkins |
|---|---|---|
| 2,015,970 A | 10/1935 | Schoene |

(Continued)

FOREIGN PATENT DOCUMENTS

| AU | 2005201364 A1 | 7/2006 |
|---|---|---|
| CA | 1094549 A | 1/1981 |

(Continued)

OTHER PUBLICATIONS

Abstract in English for JPS5684246, 1979.
(Continued)

*Primary Examiner* — Annette Dixon
(74) *Attorney, Agent, or Firm* — Paula K. Wittmayer; Philip I. Datlow

(57) ABSTRACT

An inhalation device includes: a chamber for intermediate storage of an aerosol, a first connection for a nebuliser that produces the aerosol, a second connection on a patient side for delivering the aerosol, and a third connection for breathable air, where the chamber is fluidically connected in a valve-free manner on an inlet side to the first connection when the nebuliser is attached, and the chamber is connected to the third connection in parallel on the inlet side via an inlet valve so that the breathable air from the third connection flows into the chamber.

14 Claims, 15 Drawing Sheets

(51) Int. Cl.
*A61M 15/00* (2006.01)
*A61M 16/20* (2006.01)
*A61M 11/00* (2006.01)
*A61M 16/12* (2006.01)
*B05B 11/00* (2006.01)

(52) U.S. Cl.
CPC ........ *A61M 11/06* (2013.01); *A61M 15/0013* (2014.02); *A61M 15/0018* (2014.02); *A61M 15/0021* (2014.02); *A61M 15/0065* (2013.01); *A61M 16/0816* (2013.01); *A61M 16/208* (2013.01); *A61M 16/12* (2013.01); *B05B 11/0043* (2013.01); *B05B 11/3001* (2013.01); *B05B 11/309* (2013.01); *B05B 11/3067* (2013.01); *B05B 11/3091* (2013.01)

(58) Field of Classification Search
CPC ........ A61M 15/002–15/0026; A61M 15/0065; A61M 15/0086; A61M 15/0091; A61M 15/0093–15/0096; A61M 16/00; A61M 16/08; A61M 16/0808; A61M 16/0816–16/0891; A61M 16/10; A61M 16/104–16/1045; A61M 16/16; A61M 16/18–16/209
USPC ............. 128/200.11–200.24, 202.27, 203.12, 128/203.15, 203.16, 203.17, 203.25, 128/203.26, 203.27, 204.18, 204.21, 128/205.24, 205.25, 207.14, 912
See application file for complete search history.

(56) References Cited

U.S. PATENT DOCUMENTS

| | | |
|---|---|---|
| 2,127,401 A | 8/1938 | Gillican |
| 2,161,071 A | 6/1939 | McGrath et al. |
| 2,321,428 A | 6/1943 | Schloz |
| 2,329,311 A | 9/1943 | Waters |
| 2,362,103 A | 11/1944 | Smith |
| 2,651,303 A | 9/1953 | Johnson et al. |
| 2,720,969 A | 10/1955 | Kendall |
| 2,793,776 A | 5/1957 | Lipari |
| 2,974,880 A | 3/1961 | Stewart et al. |
| 3,032,823 A | 5/1962 | Sherman et al. |
| 3,157,179 A | 11/1964 | Allen et al. |
| 3,172,568 A | 3/1965 | Modderno |
| 3,196,587 A | 7/1965 | Hayward et al. |
| 3,223,289 A | 12/1965 | Bouet |
| 3,299,603 A | 1/1967 | Shaw |
| 3,354,883 A | 11/1967 | Southerland |
| 3,440,144 A | 4/1969 | Anderson et al. |
| 3,457,694 A | 7/1969 | Tatibana |
| 3,491,803 A | 1/1970 | Galik |
| 3,502,035 A | 3/1970 | Fedit |
| 3,580,249 A | 5/1971 | Takaoka |
| 3,590,557 A | 7/1971 | Vogel |
| 3,632,743 A | 1/1972 | Geller et al. |
| 3,655,096 A | 4/1972 | Easter |
| 3,674,060 A | 7/1972 | Ruekberg |
| 3,675,825 A | 7/1972 | Morane |
| 3,802,604 A | 4/1974 | Morane et al. |
| 3,820,698 A | 6/1974 | Franz |
| 3,842,836 A | 10/1974 | Ogle |
| 3,858,580 A | 1/1975 | Ogle |
| 3,861,851 A | 1/1975 | Schiemann |
| 3,870,147 A | 3/1975 | Orth |
| 3,924,741 A | 12/1975 | Kachur et al. |
| 3,933,279 A | 1/1976 | Maier |
| 3,946,732 A | 3/1976 | Hurscham |
| 3,949,751 A | 4/1976 | Birch et al. |
| 3,951,310 A | 4/1976 | Steiman |
| 3,953,995 A | 5/1976 | Haswell et al. |
| 3,973,603 A | 8/1976 | Franz |
| 4,012,472 A | 3/1977 | Lindsey |
| 4,031,892 A | 6/1977 | Hurschman |
| 4,036,439 A | 7/1977 | Green |
| 4,048,997 A | 9/1977 | Raghavachari et al. |
| 4,067,499 A | 1/1978 | Cohen |
| 4,094,317 A | 6/1978 | Wasnich |
| 4,126,559 A | 11/1978 | Cooper |
| 4,153,689 A | 5/1979 | Hirai et al. |
| 4,174,035 A | 11/1979 | Wiegner |
| 4,177,938 A | 12/1979 | Brina |
| 4,178,928 A | 12/1979 | Tischlinger |
| 4,195,730 A | 4/1980 | Hunt |
| 4,245,788 A | 1/1981 | Wright |
| 4,275,840 A | 6/1981 | Staar |
| 4,315,570 A | 2/1982 | Silver et al. |
| 4,338,765 A | 7/1982 | Ohmori et al. |
| 4,377,106 A | 3/1983 | Workman et al. |
| 4,456,016 A | 6/1984 | Nowacki et al. |
| 4,467,965 A | 8/1984 | Skinner |
| 4,476,116 A | 10/1984 | Anik |
| 4,515,586 A | 5/1985 | Mendenhall et al. |
| 4,516,967 A | 5/1985 | Kopfer |
| 4,603,794 A | 8/1986 | DeFord et al. |
| 4,677,975 A | 7/1987 | Edgar et al. |
| 4,727,985 A | 3/1988 | McNeirney et al. |
| 4,749,082 A | 6/1988 | Gardiner et al. |
| 4,796,614 A | 1/1989 | Nowacki et al. |
| 4,805,377 A | 2/1989 | Carter |
| 4,813,210 A | 3/1989 | Masuda et al. |
| 4,821,923 A | 4/1989 | Skorka |
| 4,840,017 A | 6/1989 | Miller et al. |
| 4,863,720 A | 9/1989 | Burghart et al. |
| 4,868,582 A | 9/1989 | Dreinhoff |
| 4,885,164 A | 12/1989 | Thurow |
| 4,905,450 A | 3/1990 | Hansen et al. |
| 4,926,613 A | 5/1990 | Hansen |
| 4,951,661 A * | 8/1990 | Sladek ............... A61M 16/0808 128/202.27 |
| 4,952,310 A | 8/1990 | McMahan et al. |
| 4,964,540 A | 10/1990 | Katz |
| RE33,444 E | 11/1990 | Lerner |
| 4,973,318 A | 11/1990 | Holm et al. |
| 4,979,941 A | 12/1990 | Ogle, II |
| 4,982,875 A | 1/1991 | Pozzi et al. |
| 5,014,492 A | 5/1991 | Fiorini et al. |
| 5,025,957 A | 6/1991 | Ranalletta et al. |
| 5,059,187 A | 10/1991 | Sperry et al. |
| 5,060,791 A | 10/1991 | Zulauf |
| 5,067,655 A | 11/1991 | Farago et al. |
| 5,156,918 A | 10/1992 | Marks et al. |
| 5,174,366 A | 12/1992 | Nagakura et al. |
| 5,207,217 A | 5/1993 | Cocozza et al. |
| 5,230,884 A | 7/1993 | Evans et al. |
| 5,237,797 A | 8/1993 | Varlet |
| 5,246,142 A | 9/1993 | DiPalma et al. |
| 5,261,565 A | 11/1993 | Drobish et al. |
| 5,263,842 A | 11/1993 | Fealey |
| 5,271,153 A | 12/1993 | Reiboldt et al. |
| 5,282,304 A | 2/1994 | Reiboldt et al. |
| 5,282,549 A | 2/1994 | Scholz et al. |
| 5,284,133 A | 2/1994 | Burns et al. |
| 5,289,948 A | 3/1994 | Moss et al. |
| 5,339,990 A | 8/1994 | Wilder |
| 5,352,196 A | 10/1994 | Haber et al. |
| 5,380,281 A | 1/1995 | Tomellini et al. |
| 5,385,140 A | 1/1995 | Smith |
| 5,394,866 A | 3/1995 | Ritson et al. |
| 5,408,994 A | 4/1995 | Wass et al. |
| 5,433,343 A | 7/1995 | Meshberg |
| 5,435,282 A | 7/1995 | Haber et al. |
| 5,435,884 A | 7/1995 | Simmons et al. |
| 5,451,569 A | 9/1995 | Wong et al. |
| 5,456,522 A | 10/1995 | Beach |
| 5,456,533 A | 10/1995 | Streiff et al. |
| 5,472,143 A | 12/1995 | Bartels et al. |
| 5,482,030 A | 1/1996 | Klein |
| 5,487,378 A | 1/1996 | Robertson et al. |
| 5,497,944 A | 3/1996 | Weston et al. |
| 5,499,750 A | 3/1996 | Manifold |
| 5,499,751 A | 3/1996 | Meyer |

(56) References Cited

U.S. PATENT DOCUMENTS

| | | |
|---|---|---|
| 5,503,869 A | 4/1996 | Van Oort |
| 5,509,404 A | 4/1996 | Lloyd et al. |
| 5,518,147 A | 5/1996 | Peterson et al. |
| 5,533,994 A | 7/1996 | Meyer |
| 5,541,569 A | 7/1996 | Jang |
| 5,544,646 A | 8/1996 | Lloyd et al. |
| 5,547,094 A | 8/1996 | Bartels et al. |
| 5,569,191 A | 10/1996 | Meyer |
| 5,574,006 A | 11/1996 | Yanagawa |
| 5,579,760 A | 12/1996 | Kohler |
| 5,584,285 A * | 12/1996 | Salter ............... A61M 11/06 128/200.21 |
| 5,593,069 A | 1/1997 | Jinks |
| 5,599,297 A | 2/1997 | Chin et al. |
| 5,603,943 A | 2/1997 | Yanagawa |
| 5,614,172 A | 3/1997 | Geimer |
| 5,622,162 A | 4/1997 | Johansson et al. |
| 5,622,163 A | 4/1997 | Jewett et al. |
| 5,643,868 A | 7/1997 | Weiner et al. |
| 5,662,098 A | 9/1997 | Yoshida |
| 5,662,271 A | 9/1997 | Weston et al. |
| 5,676,930 A | 10/1997 | Jager et al. |
| 5,685,846 A | 11/1997 | Michaels, Jr. |
| 5,697,242 A | 12/1997 | Halasz et al. |
| 5,709,202 A | 1/1998 | Lloyd et al. |
| 5,722,598 A | 3/1998 | Werding |
| 5,738,087 A | 4/1998 | King |
| 5,740,967 A | 4/1998 | Simmons et al. |
| 5,763,396 A | 6/1998 | Weiner et al. |
| 5,775,321 A | 7/1998 | Alband |
| 5,782,345 A | 7/1998 | Guasch et al. |
| 5,827,262 A | 10/1998 | Neftel et al. |
| 5,829,435 A | 11/1998 | Rubsamen et al. |
| 5,833,088 A | 11/1998 | Kladders et al. |
| 5,848,588 A | 12/1998 | Foley |
| 5,868,287 A | 2/1999 | Kurokawa et al. |
| 5,881,718 A | 3/1999 | Mortensen et al. |
| 5,884,620 A | 3/1999 | Gonda et al. |
| 5,902,298 A | 5/1999 | Niedospial, Jr. et al. |
| 5,934,272 A | 8/1999 | Lloyd et al. |
| 5,935,101 A | 8/1999 | Kato et al. |
| 5,941,244 A | 8/1999 | Yamazaki et al. |
| 5,950,016 A | 9/1999 | Tanaka |
| 5,950,403 A | 9/1999 | Yamaguchi et al. |
| 5,951,882 A | 9/1999 | Simmons et al. |
| 5,964,416 A | 10/1999 | Jaeger et al. |
| 5,975,370 A | 11/1999 | Durliat |
| 5,997,263 A | 12/1999 | Van Lintel et al. |
| 6,041,777 A * | 3/2000 | Faithfull ............ A61M 16/0054 128/200.24 |
| 6,041,969 A | 3/2000 | Parise |
| 6,053,368 A | 4/2000 | Geimer |
| 6,062,430 A | 5/2000 | Fuchs |
| 6,098,618 A | 8/2000 | Jennings et al. |
| 6,109,479 A | 8/2000 | Ruckdeschel |
| 6,110,247 A | 8/2000 | Birmingham et al. |
| 6,116,233 A | 9/2000 | Denyer |
| 6,119,853 A | 9/2000 | Garrill et al. |
| 6,120,492 A | 9/2000 | Finch et al. |
| 6,123,068 A | 9/2000 | Lloyd et al. |
| 6,131,566 A | 10/2000 | Ashurst et al. |
| 6,145,703 A | 11/2000 | Opperman |
| 6,149,054 A | 11/2000 | Cirrillo et al. |
| 6,152,296 A | 11/2000 | Shih |
| 6,171,972 B1 | 1/2001 | Mehregany et al. |
| 6,176,442 B1 | 1/2001 | Eicher et al. |
| 6,179,118 B1 | 1/2001 | Garrill et al. |
| 6,186,409 B1 | 2/2001 | Srinath et al. |
| 6,199,766 B1 | 3/2001 | Fox et al. |
| 6,223,933 B1 | 5/2001 | Hochrainer et al. |
| 6,224,568 B1 | 5/2001 | Morimoto et al. |
| 6,237,589 B1 | 5/2001 | Denyer et al. |
| 6,259,654 B1 | 7/2001 | de la Huerga |
| 6,267,154 B1 | 7/2001 | Felicelli et al. |
| 6,279,786 B1 | 8/2001 | de Pous et al. |
| 6,302,101 B1 | 10/2001 | Py |
| 6,315,173 B1 | 11/2001 | Di Giovanni et al. |
| 6,319,943 B1 | 11/2001 | Joshi et al. |
| 6,336,453 B1 | 1/2002 | Scarrott et al. |
| 6,341,718 B1 | 1/2002 | Schilthuizen et al. |
| 6,349,856 B1 | 2/2002 | Chastel |
| 6,352,152 B1 | 3/2002 | Anderson et al. |
| 6,352,181 B1 | 3/2002 | Eberhard et al. |
| 6,363,932 B1 * | 4/2002 | Forchione ............ A61M 15/0086 128/200.14 |
| 6,375,048 B1 | 4/2002 | van der Meer et al. |
| 6,392,962 B1 | 5/2002 | Wyatt |
| 6,395,331 B1 | 5/2002 | Yan et al. |
| 6,401,710 B1 | 6/2002 | Scheuch et al. |
| 6,401,987 B1 | 6/2002 | Oechsel et al. |
| 6,402,055 B1 | 6/2002 | Jaeger et al. |
| 6,405,872 B1 | 6/2002 | Ruther et al. |
| 6,412,659 B1 | 7/2002 | Kneer |
| 6,419,167 B1 | 7/2002 | Fuchs |
| 6,423,298 B2 | 7/2002 | McNamara et al. |
| 6,427,682 B1 | 8/2002 | Klimowicz et al. |
| 6,446,054 B1 | 9/2002 | Mayorga Lopez |
| 6,457,658 B2 | 10/2002 | Srinath et al. |
| 6,464,108 B2 | 10/2002 | Corba |
| 6,481,435 B2 | 11/2002 | Hochrainer et al. |
| 6,491,897 B1 | 12/2002 | Freund et al. |
| 6,503,362 B1 | 1/2003 | Bartels et al. |
| 6,513,519 B2 | 2/2003 | Gallem |
| 6,543,448 B1 | 4/2003 | Smith et al. |
| 6,548,647 B2 | 4/2003 | Dietz et al. |
| 6,550,477 B1 | 4/2003 | Casper et al. |
| 6,565,743 B1 | 5/2003 | Poirier et al. |
| 6,578,741 B2 | 6/2003 | Ritsche et al. |
| 6,581,596 B1 | 6/2003 | Truitt et al. |
| 6,584,976 B2 | 7/2003 | Japuntich et al. |
| 6,606,990 B2 | 8/2003 | Stapleton et al. |
| 6,620,438 B2 | 9/2003 | Pairet et al. |
| 6,626,309 B1 | 9/2003 | Jansen et al. |
| 6,640,805 B2 | 11/2003 | Castro et al. |
| 6,641,782 B1 | 11/2003 | Mauchan et al. |
| 6,669,176 B2 | 12/2003 | Rock |
| 6,679,254 B1 | 1/2004 | Rand et al. |
| 6,685,691 B1 | 2/2004 | Freund et al. |
| 6,698,421 B2 | 3/2004 | Attolini |
| 6,706,726 B2 | 3/2004 | Meissner et al. |
| 6,708,846 B1 | 3/2004 | Fuchs et al. |
| 6,725,858 B2 | 4/2004 | Loescher |
| 6,729,328 B2 | 5/2004 | Goldemann |
| 6,732,731 B1 | 5/2004 | Tseng |
| 6,745,763 B2 | 6/2004 | Webb |
| 6,779,520 B2 | 8/2004 | Genova et al. |
| 6,789,702 B2 | 9/2004 | O'Connor et al. |
| 6,792,945 B2 | 9/2004 | Davies et al. |
| 6,823,862 B2 | 11/2004 | McNaughton |
| 6,825,441 B2 | 11/2004 | Katooka et al. |
| 6,846,413 B1 | 1/2005 | Kadel et al. |
| 6,866,039 B1 | 3/2005 | Wright et al. |
| 6,889,690 B2 | 5/2005 | Crowder et al. |
| 6,890,517 B2 | 5/2005 | Drechsel et al. |
| 6,915,901 B2 | 7/2005 | Feinberg et al. |
| 6,929,004 B1 | 8/2005 | Bonney et al. |
| 6,932,962 B1 | 8/2005 | Backstrom et al. |
| 6,942,127 B2 | 9/2005 | Raats |
| 6,964,759 B2 | 11/2005 | Lewis et al. |
| 6,977,042 B2 | 12/2005 | Kadel et al. |
| 6,978,916 B2 | 12/2005 | Smith |
| 6,986,346 B2 | 1/2006 | Hochrainer et al. |
| 6,988,496 B1 | 1/2006 | Eicher et al. |
| 6,994,083 B2 | 2/2006 | Foley et al. |
| 7,040,311 B2 | 5/2006 | Hochrainer et al. |
| 7,066,408 B2 | 6/2006 | Sugimoto et al. |
| 7,090,093 B2 | 8/2006 | Hochrainer et al. |
| 7,131,441 B1 | 11/2006 | Keller et al. |
| 7,258,716 B2 | 8/2007 | Shekarriz et al. |
| 7,314,187 B2 | 1/2008 | Hochrainer et al. |
| 7,331,340 B2 | 2/2008 | Barney |
| 7,341,208 B2 | 3/2008 | Peters et al. |
| 7,380,575 B2 | 6/2008 | Stricklin |
| 7,417,051 B2 | 8/2008 | Banholzer et al. |

(56) References Cited

U.S. PATENT DOCUMENTS

| | | |
|---|---|---|
| 7,451,876 B2 | 11/2008 | Bossi et al. |
| 7,470,422 B2 | 12/2008 | Freund et al. |
| 7,556,037 B2 | 7/2009 | Klein |
| 7,559,597 B2 | 7/2009 | Mori |
| 7,571,722 B2 | 8/2009 | Wuttke et al. |
| 7,579,358 B2 | 8/2009 | Boeck et al. |
| 7,611,694 B2 | 11/2009 | Schmidt |
| 7,611,709 B2 | 11/2009 | Bassarab et al. |
| 7,621,266 B2 | 11/2009 | Kladders et al. |
| 7,645,383 B2 | 1/2010 | Kadel et al. |
| 7,652,030 B2 | 1/2010 | Moesgaard et al. |
| 7,665,461 B2 | 2/2010 | Zierenberg et al. |
| 7,681,811 B2 | 3/2010 | Geser et al. |
| 7,686,014 B2 | 3/2010 | Boehm et al. |
| 7,717,299 B2 | 5/2010 | Greiner-Perth |
| 7,723,306 B2 | 5/2010 | Bassarab et al. |
| 7,743,945 B2 | 6/2010 | Lu et al. |
| 7,779,838 B2 | 8/2010 | Hetzer et al. |
| 7,802,568 B2 | 9/2010 | Eicher et al. |
| 7,819,342 B2 | 10/2010 | Spallek et al. |
| 7,823,584 B2 | 11/2010 | Geser et al. |
| 7,837,235 B2 | 11/2010 | Geser et al. |
| 7,849,851 B2 | 12/2010 | Zierenberg et al. |
| 7,896,264 B2 | 3/2011 | Eicher et al. |
| 7,980,243 B2 | 7/2011 | Hochrainer |
| 7,994,188 B2 | 8/2011 | Disse |
| 3,062,626 A1 | 11/2011 | Freund et al. |
| 8,167,171 B2 | 5/2012 | Moretti |
| 8,479,725 B2 | 7/2013 | Hausmann et al. |
| 8,495,901 B2 | 7/2013 | Hahn et al. |
| 8,650,840 B2 | 2/2014 | Holakovsky et al. |
| 8,651,338 B2 | 2/2014 | Leak et al. |
| 8,656,910 B2 | 2/2014 | Boeck et al. |
| 8,733,341 B2 | 5/2014 | Boeck et al. |
| 8,734,392 B2 | 5/2014 | Stadelhofer |
| 8,950,393 B2 | 2/2015 | Holakovsky et al. |
| 8,960,188 B2 | 2/2015 | Bach et al. |
| 8,997,735 B2 | 4/2015 | Zierenberg et al. |
| 9,027,854 B2 | 5/2015 | Moser et al. |
| 9,192,734 B2 | 11/2015 | Hausmann et al. |
| 9,238,031 B2 | 1/2016 | Schmelzer et al. |
| 2001/0008632 A1 | 7/2001 | Freund et al. |
| 2001/0028308 A1 | 10/2001 | De La Huerga |
| 2001/0032643 A1 | 10/2001 | Hochrainer et al. |
| 2001/0035182 A1 | 11/2001 | Rubin et al. |
| 2002/0000225 A1 | 1/2002 | Schuler et al. |
| 2002/0005195 A1 | 1/2002 | Shick et al. |
| 2002/0007155 A1 | 1/2002 | Freund et al. |
| 2002/0046751 A1 | 4/2002 | MacRae |
| 2002/0060255 A1 | 5/2002 | Benoist |
| 2002/0074429 A1 | 6/2002 | Hettrich et al. |
| 2002/0079285 A1 | 6/2002 | Jansen et al. |
| 2002/0092523 A1 | 7/2002 | Connelly et al. |
| 2002/0111363 A1 | 8/2002 | Drechsel et al. |
| 2002/0129812 A1 | 9/2002 | Litherland et al. |
| 2002/0137764 A1 | 9/2002 | Drechsel et al. |
| 2002/0176788 A1 | 11/2002 | Moutafis et al. |
| 2003/0039915 A1 | 2/2003 | Holt et al. |
| 2003/0064032 A1 | 4/2003 | Lamche et al. |
| 2003/0066524 A1 | 4/2003 | Hochrainer et al. |
| 2003/0085254 A1 | 5/2003 | Katooka et al. |
| 2003/0098023 A1 | 5/2003 | Drachmann |
| 2003/0106827 A1 | 6/2003 | Cheu et al. |
| 2003/0145849 A1 | 8/2003 | Drinan et al. |
| 2003/0178020 A1 | 9/2003 | Scarrott |
| 2003/0181478 A1 | 9/2003 | Drechsel et al. |
| 2003/0183225 A1 | 10/2003 | Knudsen |
| 2003/0187387 A1 | 10/2003 | Wirt et al. |
| 2003/0191151 A1 | 10/2003 | Chaudry et al. |
| 2003/0194379 A1 | 10/2003 | Brugger et al. |
| 2003/0196660 A1* | 10/2003 | Haveri ............ A61M 15/0085 128/203.12 |
| 2003/0209238 A1 | 11/2003 | Peters et al. |
| 2003/0226907 A1 | 12/2003 | Geser et al. |
| 2004/0004138 A1 | 1/2004 | Hettrich et al. |
| 2004/0010239 A1 | 1/2004 | Hochrainer et al. |
| 2004/0015126 A1 | 1/2004 | Zierenberg et al. |
| 2004/0019073 A1 | 1/2004 | Drechsel et al. |
| 2004/0055907 A1 | 3/2004 | Marco |
| 2004/0060476 A1 | 4/2004 | Sirejacob |
| 2004/0069799 A1 | 4/2004 | Gee et al. |
| 2004/0092428 A1 | 5/2004 | Chen et al. |
| 2004/0094147 A1 | 5/2004 | Schyra et al. |
| 2004/0134494 A1 | 7/2004 | Papania et al. |
| 2004/0134824 A1 | 7/2004 | Chan et al. |
| 2004/0139700 A1 | 7/2004 | Powell et al. |
| 2004/0143235 A1 | 7/2004 | Freund et al. |
| 2004/0166065 A1 | 8/2004 | Schmidt |
| 2004/0182867 A1 | 9/2004 | Hochrainer et al. |
| 2004/0184994 A1 | 9/2004 | DeStefano et al. |
| 2004/0194524 A1 | 10/2004 | Jentzsch |
| 2004/0210199 A1 | 10/2004 | Atterbury et al. |
| 2004/0231667 A1 | 11/2004 | Horton et al. |
| 2005/0028815 A1 | 2/2005 | Deaton et al. |
| 2005/0028816 A1 | 2/2005 | Fishman et al. |
| 2005/0061314 A1 | 3/2005 | Davies et al. |
| 2005/0089478 A1 | 4/2005 | Govind et al. |
| 2005/0098172 A1 | 5/2005 | Anderson |
| 2005/0126469 A1 | 6/2005 | Lu |
| 2005/0131357 A1 | 6/2005 | Denton et al. |
| 2005/0158394 A1 | 7/2005 | Staniforth et al. |
| 2005/0159441 A1 | 7/2005 | Hochrainer et al. |
| 2005/0183718 A1 | 8/2005 | Wuttke et al. |
| 2005/0191246 A1 | 9/2005 | Bechtold-Peters et al. |
| 2005/0194472 A1 | 9/2005 | Geser et al. |
| 2005/0239778 A1 | 10/2005 | Konetzki et al. |
| 2005/0247305 A1 | 11/2005 | Zierenberg et al. |
| 2005/0250704 A1 | 11/2005 | Bassarab et al. |
| 2005/0250705 A1 | 11/2005 | Bassarab et al. |
| 2005/0255119 A1 | 11/2005 | Bassarab et al. |
| 2005/0263618 A1 | 12/2005 | Spallek et al. |
| 2005/0268909 A1 | 12/2005 | Bonney et al. |
| 2005/0268915 A1 | 12/2005 | Wassenaar et al. |
| 2005/0269359 A1 | 12/2005 | Raats |
| 2006/0002863 A1 | 1/2006 | Schmelzer et al. |
| 2006/0016449 A1 | 1/2006 | Eicher et al. |
| 2006/0035874 A1 | 2/2006 | Lulla et al. |
| 2006/0037612 A1 | 2/2006 | Herder et al. |
| 2006/0067952 A1 | 3/2006 | Chen |
| 2006/0086828 A1 | 4/2006 | Bougamont et al. |
| 2006/0150971 A1 | 7/2006 | Lee et al. |
| 2006/0196500 A1 | 9/2006 | Hochrainer et al. |
| 2006/0225734 A1 | 10/2006 | Sagaser et al. |
| 2006/0239930 A1 | 10/2006 | Lamche et al. |
| 2006/0254579 A1 | 11/2006 | Grychowski et al. |
| 2006/0279588 A1 | 12/2006 | Yearworth et al. |
| 2006/0282045 A1 | 12/2006 | Wilkinson et al. |
| 2006/0285987 A1 | 12/2006 | Jaeger et al. |
| 2006/0289002 A1 | 12/2006 | Hetzer et al. |
| 2006/0293293 A1 | 12/2006 | Muller et al. |
| 2007/0062518 A1 | 3/2007 | Geser et al. |
| 2007/0062519 A1 | 3/2007 | Wuttke et al. |
| 2007/0062979 A1 | 3/2007 | Dunne |
| 2007/0090205 A1 | 4/2007 | Kunze et al. |
| 2007/0090576 A1 | 4/2007 | Geser et al. |
| 2007/0107720 A1 | 5/2007 | Boeck et al. |
| 2007/0119449 A1 | 5/2007 | Boehm et al. |
| 2007/0137643 A1 | 6/2007 | Bonney et al. |
| 2007/0163574 A1 | 7/2007 | Rohrschneider et al. |
| 2007/0183982 A1 | 8/2007 | Berkel et al. |
| 2007/0210121 A1 | 9/2007 | Stadelhofer et al. |
| 2007/0221211 A1 | 9/2007 | Sagalovich |
| 2007/0272763 A1 | 11/2007 | Dunne et al. |
| 2007/0298116 A1 | 12/2007 | Bechtold-Peters et al. |
| 2008/0017192 A1 | 1/2008 | Southby et al. |
| 2008/0029085 A1 | 2/2008 | Lawrence et al. |
| 2008/0060640 A1* | 3/2008 | Waldner ............ A61M 15/0085 128/200.16 |
| 2008/0083408 A1 | 4/2008 | Hodson et al. |
| 2008/0092885 A1 | 4/2008 | von Schuckmann |
| 2008/0156321 A1 | 7/2008 | Bowman et al. |
| 2008/0197045 A1 | 8/2008 | Metzger et al. |
| 2008/0249459 A1 | 10/2008 | Godfrey et al. |
| 2008/0264412 A1 | 10/2008 | Meyer et al. |

(56) References Cited

U.S. PATENT DOCUMENTS

| | | |
|---|---|---|
| 2008/0265198 A1 | 10/2008 | Warby |
| 2008/0283553 A1 | 11/2008 | Cox et al. |
| 2008/0299049 A1* | 12/2008 | Stangl ............... A61M 15/0085 424/45 |
| 2008/0308580 A1 | 12/2008 | Gaydos et al. |
| 2009/0032427 A1 | 2/2009 | Cheu et al. |
| 2009/0060764 A1 | 3/2009 | Mitzlaff et al. |
| 2009/0075990 A1 | 3/2009 | Schmidt |
| 2009/0114215 A1 | 5/2009 | Boeck et al. |
| 2009/0166379 A1 | 7/2009 | Wright et al. |
| 2009/0170839 A1 | 7/2009 | Schmidt |
| 2009/0185983 A1 | 7/2009 | Freund et al. |
| 2009/0197841 A1 | 8/2009 | Kreher et al. |
| 2009/0202447 A1 | 8/2009 | Kreher et al. |
| 2009/0211576 A1 | 8/2009 | Lehtonen et al. |
| 2009/0221626 A1 | 9/2009 | Schmidt |
| 2009/0235924 A1 | 9/2009 | Holakovsky et al. |
| 2009/0272664 A1 | 11/2009 | Marshall et al. |
| 2009/0293870 A1 | 12/2009 | Brunnberg et al. |
| 2009/0306065 A1 | 12/2009 | Schmidt |
| 2009/0308772 A1 | 12/2009 | Abrams |
| 2009/0314287 A1 | 12/2009 | Spallek et al. |
| 2009/0317337 A1 | 12/2009 | Schmidt |
| 2010/0018524 A1 | 1/2010 | Jinks et al. |
| 2010/0018997 A1 | 1/2010 | Faneca Llesera |
| 2010/0044393 A1 | 2/2010 | Moretti |
| 2010/0056559 A1 | 3/2010 | Schmelzer et al. |
| 2010/0084531 A1 | 4/2010 | Schuchman |
| 2010/0095957 A1 | 4/2010 | Corbacho |
| 2010/0144784 A1 | 6/2010 | Schmelzer et al. |
| 2010/0168710 A1 | 7/2010 | Braithwaite |
| 2010/0237102 A1 | 9/2010 | Margheritis |
| 2010/0242557 A1 | 9/2010 | Spreitzer et al. |
| 2010/0242954 A1 | 9/2010 | Hahn et al. |
| 2010/0313884 A1 | 12/2010 | Elliman |
| 2011/0005517 A1 | 1/2011 | Boeck et al. |
| 2011/0041842 A1 | 2/2011 | Bradshaw et al. |
| 2011/0168175 A1 | 7/2011 | Dunne et al. |
| 2011/0239594 A1 | 10/2011 | Nottingham et al. |
| 2011/0245780 A1 | 10/2011 | Helmer et al. |
| 2011/0268668 A1 | 11/2011 | Lamche et al. |
| 2011/0277753 A1 | 11/2011 | Dunne et al. |
| 2011/0290239 A1 | 12/2011 | Bach et al. |
| 2011/0290242 A1 | 12/2011 | Bach et al. |
| 2011/0290243 A1 | 12/2011 | Bach et al. |
| 2012/0090603 A1 | 4/2012 | Dunne et al. |
| 2012/0132199 A1 | 5/2012 | Kiesewetter |
| 2012/0138049 A1 | 6/2012 | Wachtel |
| 2012/0138713 A1 | 6/2012 | Schuy et al. |
| 2012/0260913 A1 | 10/2012 | Bach et al. |
| 2012/0325204 A1 | 12/2012 | Holakovsky et al. |
| 2013/0012908 A1 | 1/2013 | Yeung |
| 2013/0056888 A1 | 3/2013 | Holakovsky et al. |
| 2013/0125880 A1 | 5/2013 | Holakovsky et al. |
| 2013/0125881 A1 | 5/2013 | Holakovsky et al. |
| 2013/0126389 A1 | 5/2013 | Holakovsky et al. |
| 2013/0206136 A1 | 8/2013 | Herrmann et al. |
| 2013/0269687 A1 | 10/2013 | Besseler et al. |
| 2014/0121234 A1 | 5/2014 | Kreher et al. |
| 2014/0190472 A1 | 7/2014 | Holakovsky et al. |
| 2014/0228397 A1 | 8/2014 | Schmelzer et al. |
| 2014/0331994 A1 | 11/2014 | Holakovsky et al. |
| 2015/0040890 A1 | 2/2015 | Besseler et al. |
| 2015/0040893 A1 | 2/2015 | Besseler et al. |
| 2015/0041558 A1 | 2/2015 | Besseler et al. |
| 2015/0114387 A1 | 4/2015 | Bach et al. |
| 2015/0122247 A1 | 5/2015 | Besseler et al. |
| 2015/0258021 A1 | 9/2015 | Kreher et al. |
| 2015/0306087 A1 | 10/2015 | Schmelzer et al. |
| 2015/0320947 A1 | 11/2015 | Eicher et al. |
| 2015/0320948 A1 | 11/2015 | Eicher et al. |

FOREIGN PATENT DOCUMENTS

| | | |
|---|---|---|
| CA | 2233981 A1 | 4/1997 |
| CA | 2237853 A1 | 6/1997 |
| CA | 2251828 A1 | 10/1997 |
| CA | 2275392 A1 | 7/1998 |
| CA | 2297174 A1 | 2/1999 |
| CA | 2343123 A1 | 4/2000 |
| CA | 2434872 A1 | 8/2002 |
| CA | 2497059 A1 | 3/2004 |
| CA | 2497680 A1 | 3/2004 |
| CA | 2513167 A1 | 10/2004 |
| CA | 2557020 A1 | 9/2005 |
| CA | 2653183 A1 | 12/2007 |
| CA | 2653422 A1 | 12/2007 |
| CN | 1125426 A | 6/1996 |
| CN | 1849174 A | 10/2006 |
| CN | 101247897 A | 8/2008 |
| DE | 1653651 A1 | 7/1971 |
| DE | 2754100 A1 | 6/1978 |
| DE | 4117078 A1 | 11/1992 |
| DE | 19625027 A1 | 1/1997 |
| DE | 19615422 A1 | 11/1997 |
| DE | 19653969 A1 | 6/1998 |
| DE | 19902844 C1 | 11/1999 |
| DE | 10007591 A1 | 11/2000 |
| DE | 10104367 A1 | 8/2002 |
| DE | 10300983 A1 | 7/2004 |
| DE | 102004031673 A1 | 1/2006 |
| DE | 202006017793 U1 | 1/2007 |
| DE | 01102006025871 A1 | 12/2007 |
| DK | 83175 C | 7/1957 |
| DK | 140801 B | 11/1979 |
| EP | 0018609 A1 | 11/1980 |
| EP | 0289332 A1 | 11/1988 |
| EP | 0289336 A2 | 11/1988 |
| EP | 0354507 A2 | 2/1990 |
| EP | 0364235 A1 | 4/1990 |
| EP | 0372777 A2 | 6/1990 |
| EP | 0386800 A1 | 9/1990 |
| EP | 0412524 A1 | 2/1991 |
| EP | 0505123 A1 | 9/1992 |
| EP | 0520571 A1 | 12/1992 |
| EP | 0622311 A2 | 11/1994 |
| EP | 0642992 A2 | 3/1995 |
| EP | 0679443 A1 | 11/1995 |
| EP | 0735048 A1 | 10/1996 |
| EP | 0778221 A1 | 6/1997 |
| EP | 0845253 A2 | 6/1998 |
| EP | 0845265 A1 | 6/1998 |
| EP | 0860210 A2 | 8/1998 |
| EP | 0916428 A2 | 5/1999 |
| EP | 0965355 A2 | 12/1999 |
| EP | 0970751 A2 | 1/2000 |
| EP | 1003478 A1 | 5/2000 |
| EP | 1017469 A1 | 7/2000 |
| EP | 1025923 A1 | 8/2000 |
| EP | 1068906 A2 | 1/2001 |
| EP | 1075875 A2 | 2/2001 |
| EP | 1092447 A2 | 4/2001 |
| EP | 1157689 A1 | 11/2001 |
| EP | 1211628 A2 | 6/2002 |
| EP | 1245244 A2 | 10/2002 |
| EP | 1312418 A2 | 5/2003 |
| EP | 1375385 A2 | 1/2004 |
| EP | 1521609 A2 | 4/2005 |
| EP | 1535643 A1 | 6/2005 |
| EP | 1595564 A1 | 11/2005 |
| EP | 1595822 A1 | 11/2005 |
| EP | 1726324 A1 | 11/2006 |
| EP | 1736193 A1 | 12/2006 |
| EP | 1795221 A1 | 6/2007 |
| EP | 1813548 A1 | 8/2007 |
| EP | 2135632 A1 | 12/2009 |
| ES | 2262348 T3 | 11/2006 |
| FR | 2505688 A1 | 11/1982 |
| FR | 2604363 A1 | 4/1988 |
| FR | 2673608 A1 | 9/1992 |
| FR | 2756502 A1 | 6/1998 |

(56) References Cited

FOREIGN PATENT DOCUMENTS

| | | | |
|---|---|---|---|
| GB | 1524431 A | 9/1978 |
| GB | 2081396 A | 2/1982 |
| GB | 2101020 A | 1/1983 |
| GB | 2279273 A | 1/1995 |
| GB | 2291135 A | 1/1996 |
| GB | 2332372 A | 6/1999 |
| GB | 2333129 A | 7/1999 |
| GB | 2347870 A | 9/2000 |
| GB | 2355252 A | 4/2001 |
| GB | 2398253 A | 8/2004 |
| GB | 0700839.4 | 7/2008 |
| JP | S5684246 A | 7/1981 |
| JP | H01288265 A | 11/1989 |
| JP | H0228121 A | 1/1990 |
| JP | 057246 | 2/1993 |
| JP | 05-53470 A | 3/1993 |
| JP | H06312019 A | 11/1994 |
| JP | H07118164 A | 5/1995 |
| JP | H07118166 A | 5/1995 |
| JP | 07323086 A | 12/1995 |
| JP | H08277226 A | 10/1996 |
| JP | H092442 A | 1/1997 |
| JP | H0977073 A | 3/1997 |
| JP | H09315953 A | 12/1997 |
| JP | 2001518428 A | 10/2001 |
| JP | 2001346878 A | 12/2001 |
| JP | 2002504411 A | 2/2002 |
| JP | 03511212 A | 3/2003 |
| JP | 2003299717 A | 10/2003 |
| JP | 2004-502502 A | 1/2004 |
| JP | 2004097617 A | 4/2004 |
| JP | 2005511210 A | 4/2005 |
| JP | 2005144459 A | 6/2005 |
| JP | 2007517529 A | 7/2007 |
| JP | 2007245144 A | 9/2007 |
| JP | 2007534379 A | 11/2007 |
| JP | 2008119489 A | 5/2008 |
| JP | 2008541808 A | 11/2008 |
| JP | 2010526620 A | 8/2010 |
| JP | 2010540371 A | 12/2010 |
| WO | 8100674 A1 | 3/1981 |
| WO | 8200785 A1 | 3/1982 |
| WO | 8300288 A1 | 2/1983 |
| WO | 8303054 A1 | 9/1983 |
| WO | 8605419 A1 | 9/1986 |
| WO | 8706137 A1 | 10/1987 |
| WO | 8803419 A1 | 5/1988 |
| WO | 8900889 A1 | 2/1989 |
| WO | 8900947 A1 | 2/1989 |
| WO | 8902279 A1 | 3/1989 |
| WO | 8903672 A1 | 5/1989 |
| WO | 8903673 A1 | 5/1989 |
| WO | 8905139 A1 | 6/1989 |
| WO | 9009780 A1 | 9/1990 |
| WO | 9009781 A1 | 9/1990 |
| WO | 9114468 A1 | 10/1991 |
| WO | 9206704 A1 | 4/1992 |
| WO | 9217231 A1 | 10/1992 |
| WO | 9221332 A1 | 12/1992 |
| WO | 9222286 | 12/1992 |
| WO | 9313737 A1 | 7/1993 |
| WO | 9324164 A1 | 12/1993 |
| WO | 9325321 A1 | 12/1993 |
| WO | 9407607 A1 | 4/1994 |
| WO | 9417822 A1 | 8/1994 |
| WO | 9425371 A1 | 11/1994 |
| WO | 9427653 A2 | 12/1994 |
| WO | 9503034 A1 | 2/1995 |
| WO | 9532015 A1 | 11/1995 |
| WO | 9600050 A1 | 1/1996 |
| WO | 9606011 A2 | 2/1996 |
| WO | 9606581 A1 | 3/1996 |
| WO | 9623522 A1 | 8/1996 |
| WO | 9701329 A1 | 1/1997 |
| WO | 9706813 A1 | 2/1997 |
| WO | 9706842 A1 | 2/1997 |
| WO | 9712683 A1 | 4/1997 |
| WO | 9712687 A1 | 4/1997 |
| WO | 9720590 A1 | 6/1997 |
| WO | 9723208 A1 | 7/1997 |
| WO | 9727804 A1 | 8/1997 |
| WO | 9735562 A1 | 10/1997 |
| WO | 9741833 A1 | 11/1997 |
| WO | 9812511 A2 | 3/1998 |
| WO | 9827959 A2 | 7/1998 |
| WO | 9831346 A1 | 7/1998 |
| WO | 9839043 A1 | 9/1998 |
| WO | 9901227 A1 | 1/1999 |
| WO | 9907340 A1 | 2/1999 |
| WO | 9911563 A1 | 3/1999 |
| WO | 9916530 A1 | 4/1999 |
| WO | 9943571 A1 | 9/1999 |
| WO | 9962495 A2 | 12/1999 |
| WO | 9965464 | 12/1999 |
| WO | 0001612 A2 | 1/2000 |
| WO | 0023037 A1 | 4/2000 |
| WO | 0023065 A2 | 4/2000 |
| WO | 0027543 A1 | 5/2000 |
| WO | 0033965 A1 | 6/2000 |
| WO | 0037336 A1 | 6/2000 |
| WO | 0049988 A2 | 8/2000 |
| WO | 0064779 A1 | 11/2000 |
| WO | 0113885 A1 | 3/2001 |
| WO | 0128489 A1 | 4/2001 |
| WO | 0164182 A2 | 9/2001 |
| WO | 0185097 A2 | 11/2001 |
| WO | 0187392 A2 | 11/2001 |
| WO | 0197888 A2 | 12/2001 |
| WO | 0198175 A1 | 12/2001 |
| WO | 0198176 A2 | 12/2001 |
| WO | 02/04054 A1 | 1/2002 |
| WO | 0205879 A1 | 1/2002 |
| WO | 0217988 A2 | 3/2002 |
| WO | 0232899 A1 | 4/2002 |
| WO | 0234411 A1 | 5/2002 |
| WO | 02070141 A1 | 9/2002 |
| WO | 02089887 A1 | 11/2002 |
| WO | 03002045 A1 | 1/2003 |
| WO | 03014832 A1 | 2/2003 |
| WO | 03020253 A2 | 3/2003 |
| WO | 03022332 A2 | 3/2003 |
| WO | 03035030 A1 | 5/2003 |
| WO | 03037159 A2 | 5/2003 |
| WO | 03037259 A2 | 5/2003 |
| WO | 03049786 A2 | 6/2003 |
| WO | 03050031 A1 | 6/2003 |
| WO | 03053350 A2 | 7/2003 |
| WO | 03057593 A1 | 7/2003 |
| WO | 03059547 A1 | 7/2003 |
| WO | 03068299 A1 | 8/2003 |
| WO | 03087097 A1 | 10/2003 |
| WO | 03097139 A1 | 11/2003 |
| WO | 2004019985 A1 | 3/2004 |
| WO | 2004022052 A1 | 3/2004 |
| WO | 2004022132 A2 | 3/2004 |
| WO | 2004022244 A1 | 3/2004 |
| WO | 2004024157 A1 | 3/2004 |
| WO | 2004033954 A2 | 4/2004 |
| WO | 2004062813 A1 | 7/2004 |
| WO | 2004078236 A2 | 9/2004 |
| WO | 2004089551 A2 | 10/2004 |
| WO | 2004091704 A1 | 10/2004 |
| WO | 2004098689 A1 | 11/2004 |
| WO | 2005000476 A1 | 1/2005 |
| WO | 2005004844 A1 | 1/2005 |
| WO | 2005014175 A1 | 2/2005 |
| WO | 2005020953 A1 | 3/2005 |
| WO | 2005030211 A1 | 4/2005 |
| WO | 2005055976 A2 | 6/2005 |
| WO | 2005077445 A1 | 8/2005 |
| WO | 2005079997 A1 | 9/2005 |
| WO | 2005080001 A1 | 9/2005 |
| WO | 2005080002 A1 | 9/2005 |
| WO | 2005087299 A1 | 9/2005 |

(56) References Cited

FOREIGN PATENT DOCUMENTS

| | | |
|---|---|---|
| WO | 2005107837 A1 | 11/2005 |
| WO | 2005109948 A2 | 11/2005 |
| WO | 2005112892 A1 | 12/2005 |
| WO | 2005112996 A1 | 12/2005 |
| WO | 2005113007 A2 | 12/2005 |
| WO | 2006011638 A1 | 2/2006 |
| WO | 2006018392 A1 | 2/2006 |
| WO | 2006027595 A1 | 3/2006 |
| WO | 2006037636 A2 | 4/2006 |
| WO | 2006037948 A2 | 4/2006 |
| WO | 2006042297 A2 | 4/2006 |
| WO | 2006045813 A1 | 5/2006 |
| WO | 2006110080 A1 | 10/2006 |
| WO | 2006125577 A2 | 11/2006 |
| WO | 2006126014 A2 | 11/2006 |
| WO | 2007011475 A1 | 1/2007 |
| WO | 2007022898 A2 | 3/2007 |
| WO | 2007030162 A2 | 3/2007 |
| WO | 2007049239 A2 | 5/2007 |
| WO | 2007060104 A2 | 5/2007 |
| WO | 2007060105 A1 | 5/2007 |
| WO | 2007060106 A1 | 5/2007 |
| WO | 2007060107 A1 | 5/2007 |
| WO | 2007060108 A2 | 5/2007 |
| WO | 2007062721 A1 | 6/2007 |
| WO | 2007090822 A2 | 8/2007 |
| WO | 2007101557 A2 | 9/2007 |
| WO | 2007128381 A1 | 11/2007 |
| WO | 2007134965 A1 | 11/2007 |
| WO | 2007134966 A1 | 11/2007 |
| WO | 2007134967 A1 | 11/2007 |
| WO | 2007134968 A1 | 11/2007 |
| WO | 2007141201 A1 | 12/2007 |
| WO | 2007141203 A1 | 12/2007 |
| WO | 2008023017 A2 | 2/2008 |
| WO | 2008047035 A2 | 4/2008 |
| WO | 2008077623 A1 | 7/2008 |
| WO | 2008124666 A2 | 10/2008 |
| WO | 2008138936 A2 | 11/2008 |
| WO | 2008146025 A2 | 12/2008 |
| WO | 2009006137 A1 | 1/2009 |
| WO | 2009047021 A1 | 4/2009 |
| WO | 2009047173 A2 | 4/2009 |
| WO | 2009050978 A1 | 4/2009 |
| WO | 2009090245 A1 | 7/2009 |
| WO | 2009103510 A1 | 8/2009 |
| WO | 2009115200 A1 | 9/2009 |
| WO | 2010005946 A2 | 1/2010 |
| WO | 2010006870 A1 | 1/2010 |
| WO | 2010094305 A1 | 8/2010 |
| WO | 2010094413 A2 | 8/2010 |
| WO | 2010112358 A2 | 10/2010 |
| WO | 2010133294 A2 | 11/2010 |
| WO | 2011006711 A1 | 1/2011 |
| WO | 2011064160 A1 | 6/2011 |
| WO | 2011064163 A1 | 6/2011 |
| WO | 2011064164 A1 | 6/2011 |
| WO | 2011131779 A1 | 10/2011 |
| WO | 2011154295 A2 | 12/2011 |
| WO | 2011160932 A1 | 12/2011 |
| WO | 02012130757 A1 | 10/2012 |
| WO | 2012159914 A1 | 11/2012 |
| WO | 2012160047 A2 | 11/2012 |
| WO | 2012160052 A1 | 11/2012 |
| WO | 2012161685 A1 | 11/2012 |
| WO | 2012162305 A1 | 11/2012 |
| WO | 2013110601 A1 | 8/2013 |
| WO | 2013152861 A1 | 10/2013 |
| WO | 2013152894 A1 | 10/2013 |
| WO | 2015018901 A1 | 2/2015 |
| WO | 2015018903 A1 | 2/2015 |
| WO | 2015018904 A1 | 2/2015 |
| WO | 2015169431 A2 | 11/2015 |
| WO | 2015169732 A1 | 11/2015 |
| ZA | 199901520 A | 12/1999 |

OTHER PUBLICATIONS

Abstract in English of JPH0977073, 1997.
International Search Report for PCT/EP2009/001619 mailed Jun. 10, 2009.
International Search Report for corresponding PCT/EP2010/000796; date of mailing: Oct. 28, 2010.
Ackermann et al.; Quantitative Online Detection of Low-Concentrated Drugs via a SERS Microfluidic System; ChemPhysChem; 2007; vol. 8; No. 18; pp. 2665-2670.
Cras et al., "Comparison of chemical cleaning methods of glass in preparation for silanization". Biosensors & Bioelectronics, vol. 14, 1999, pp. 683-688.
Elwenspoek et al., "Silicon Micromachining", Chapter 3, Mechanical Microsensors, Springer-Verlag Berlin Heidelberg, 2001, 4 pages.
Han et al.; Surface activation of thin silicon oxides by wet cleaning and silanization; Thin Solid Films; 2006; vol. 510; No. 1-2; pp. 175-180.
Henkel et al.; Chip modules for generation and manipulation of fluid segments for micro serial flow processes; Chemical Engineering Journal; 2004; vol. 101; pp. 439-445.
Hoffmann et al., "Mixed self-assembled monolayers (SAMs) consisting of methoxy-tri(ethylene glycol)-terminated and alkyl-terminated dimethylchlorosilanes control the non-specific adsorption of proteins at oxidic surfaces". Journal of Colloid and Interface Science, vol. 295, 2006, pp. 427-435.
Husseini et al., "Alkyl Monolayers on Silica Surfaces Prepared Using Neat, Heated Dimethylmonochlorosilanes with Low Vapor Pressures". Langmuir, vol. 19, 2003, pp. 5169-5171.
International Search Report for PCT/EP2010/053668; date of mailing: Nov. 8, 2010.
Kutchoukov et al., "Fabrication of nanofluidic devices using glass-to-glass anodic bonding" Sensors and Actuators A, vol. 114, 2004, pp. 521-527.
Mandal et al., "Cytophobic surface modification of microfluidic arrays for in situ parallel peptide synthesis and cell adhesion assays". Biotechnology Progress, vol. 23, No. 4, 2007, pp. 972-978 (Author Manuscript Available in PMC, Sep. 21, 2009, 19 pages).
Wang et al.; Self-Assembled Silane Monolayers: Fabrication with Nanoscale Uniformity; Langmuir; 2005; vol. 21; No. 5; pp. 1848-1857.
Chen F-K et al., "A study of forming pressure in the tube-hydroforming process". Journal of Materials Processing Technology, 192-193, 2007, p. 404-409.
International Search Report and Written Opinion for PCT/EP2010/057937 mailed Jul. 20, 2010.
International Search Report and Written Opinion for PCT/EP2009/005949 mailed Jan. 20, 2010.
International Search Report and Written Opinion for PCT/EP2012/058905 mailed Oct. 19, 2012.
International Search Report and Written Opinion for PCT/EP2012/059454 mailed Jan. 14, 2013.
International Search Report and Written Opinion for PCT/EP2012/059463 mailed Oct. 25, 2012.
International Search Report and Written Opinion for PCT/EP2013/001068 mailed on Jun. 5, 2013.
International Search Report for PCT/EP2008/011112 mailed Sep. 3, 2009.
International Search Report for PCT/EP2009/001153; date of mailing: May 20, 2009.
Abstract in English of FR2604363, Sep. 30, 1986.
International Search Report and Written Opinion for PCT/EP2010/067896, mailed Apr. 13, 2011.
International Search Report and Written Opinion for PCT/EP2010/067902 mailed May 2, 2011.
International Search Report for PCT/EP2012/055209 mailed Jan. 6, 2012.
International Search Report and Written Opinion for PCT/EP2010/067901, mailed Apr. 14, 2011.
"Activate". Collins English Dictionary, London: Collins, 2000, 2 pages. [Retrieved at http://search.credoreference.com/content/entry/hcengdict/activate/0 on Jun. 12, 2014].

(56) References Cited

OTHER PUBLICATIONS

International Search Report, Form PCT/ISA/210, for corresponding PCT/EP2011/059088; date of mailing: Sep. 26, 2011.
International Search Report and Written Opinion for PCT/EP2015/000903 mailed Nov. 5, 2015.
International Search Report and Written Opinion for PCT/EP2015/059691 mailed Oct. 8, 2015.
Beasley R et al: "Preservatives in Nebulizer solutions: Risks without Benefit" Pharmacotherapy, Boston, US, Bd. 18, Nr. 1, Jan. 1998, pp. 130-139.
International Search Report and Written Opinion for PCT/EP2007/054488 mailed Jul. 18, 2007.
International Search Report and Written Opinion for PCT/EP2007/054490 mailed Jul. 17, 2007.
Beasley R et al: "Preservatives in Nebulizer solutions: Risks without Benefit" Pharmacotherapy, Boston, US, Bd. 18, Nr. 1, Jan. 1998.
JP2005144459—English language abstract only.
International Search Report and Written Opinion for PCT/EP2013/054324 mailed on Jun. 5, 2013.
International Search Report for PCT/EP2010/002740, 13 pages, mailed Nov. 12, 2010.
International Search Report and Written Opinion for PCT/EP2014/067001 mailed Sep. 9, 2014.
International Search Report and Written Opinion for PCT/EP2014/067004 mailed Jan. 10, 2014.
International Search Report and Written Opinion for PCT/EP2014/067006 mailed Nov. 24, 2014.
International Search Report for PCT/EP199804803 mailed Dec. 15, 1998.
Abstract in English for DE4117078, 1992.
International Search Report for PCT/EP1999/07589 mailed Mar. 1, 2000.
International Search Report and Written Opinion for PCT/EP04006768 mailed on Sep. 24, 2004.
International Search Report and Written Opinion for PCT/EP2005/004792 mailed on Aug. 4, 2015.
International Search Report and Written Opinion for PCT/EP2005/001947 mailed on May 19, 2005.
Abstract in English of DE10007591, 2000.
Abstract in English for DE19902844, 1999.
International Search Report and Written Opinion for PCT/EP2005/055560 mailed Mar. 2, 2006.
International Search Report and Written Opinion for PCT/EP2005/068399 mailed on Jun. 25, 2007.
International Search Report and Written Opinion for PCT/EP2006/068397 mailed Feb. 21, 2007.
International Search Report and Written Opinion for PCT/EP2006/068398 mailed on May 10, 2007.
International Search Report and Written Opinion for PCT/EP2006/068396 mailed Apr. 23, 2007.
International Search Report and Written Opinion for PCT/EP2006/068395 mailed on Jun. 25, 2007.
Remington Pharmacy, Editor Alfonso R. Gennaro. 19th ed., Spanish Secondary Edition: Panamericana, Spain, 1995, Sciarra, J.J., "Aerosols", pp. 2560-2582. The English translation is from the 1995 English Primary Edition, Sciarra, J.J., Chapter 95, R97-1185.
International Search Report PCT/EP2007/051095 mailed Sep. 21, 2007.
China Suppliers, Shanghai Lite Chemical Technology Co., Ltd. Product details on polyvinylpyrrolidones. Obtained online by the USPTO examiner on Apr. 24, 2011.
International Search Report and Written Opinion for PCT/EP2007/055381 mailed on Sep. 3, 2007.
International Search Report and Written Opinion for PCT/EP2007/055383 mailed Sep. 27, 2007.
Abstract in English of WO199839043, 1998.
Abstract in English of WO199706813, 1997.
Abstract in English of JPH09315953, 1997.
Abstract in English of JPH08277226, 1996.
Abstract in English of JPH07118164, 1995.
Abstract in English of JPH07118166, 1995.
Lougheed et al., "Insulin Aggregation in Artificial Delivery Systems". Diabetologia, vol. 19, 1980, pp. 1-9.
Abstract in English for EP0354507, 1990.
Wall et al., "High levels of exopeptidase activity are present in rat and canine bronchoalveolar lavage fluid". International Journal of Pharmaceutics, vol. 97, Issue 1-3, pp. 171-181, 1993, Abstract pp. 1-2.
Fuchs et al., "Neopterin, biochemistry and clinical use as a marker for cellular immune reactions". International Archives of Allergy and Immunology, vol. 101, No. 1, 1993, pp. 1-6, Abstract 1p.
Jendle et al., "Intrapulmonary administration of insulin to healthy volunteers". Journal of Internal Medicine, vol. 240, 1996, pp. 93-98.
Diamond et al., "Substance P Fails to Mimic Vagally Mediated Nonadrenergic Bronchodilation". Peptides, vol. 3, 1982, pp. 27-29.
Niven et al., "Some Factors Associated with the Ultrasonic Nebulization of Proteins". Pharmaceutical Research, vol. 12, No. 1, 1995, pp. 53-59.
Bocci et al., "Pulmonary catabolism of interferons: alveolar absorption of 125I-labeled human interferon alpha is accompanied by partial loss of biological activity". Antiviral Research, vol. 4, 1984, pp. 211-220.
Ip et al., "Stability of Recombinant Consensus Interferon to Air-Jet and Ultrasonic Nebulization". Journal of Pharmaceutical Sciences, vol. 84, No. 10, Oct. 1995, pp. 1210-1214.
Trasch et al., "Performance data of refloquant Glucose in the Evaluation of Reflotron". Clinical Chemistry, vol. 30, 1984, p. 969 (abstract only).
"Lung Cancer". Merck Manual Home Edition, pp. 1-7. [Accessed at www.merck.com/mmhe/print/sec04/ch057/ch057a.html, on Jul. 28, 2010].
International Search Report and Written Opinion for PCT/EP2007/001558 mailed on Sep. 28, 2007.
Abstract in English for FR2756502, 1998.
Abstract in English of WO2002070141, 2002.
International Search Report and Written Opinion for PCT/EP2007/054492 mailed on Aug. 16, 2007.
International Search Report for PCT/EP2007/054489 mailed Feb. 10, 2007.
International Search Report for PCT/EP2007/003322 mailed Aug. 17, 2007.
English Language Abstract of EP1068906, 2001.
International Search Report for PCT/EP2008/055863 mailed Dec. 19, 2008.
International Search Report and Written Opinion for PCT/EP2009/001619 mailed Jun. 10, 2009.
Abstract in English of DE202006017793, 2007.
Abstract in English of JPH092442, 1997.
Abstract in English for WO2009050978, 2009.

* cited by examiner

ADAPTER, INHALATION DEVICE, AND ATOMIZER

CROSS REFERENCE TO RELATED APPLICATIONS

This is a continuation application of U.S. patent application Ser. No. 13/321,281, issued as U.S. Pat. No. 9,265,910, which is a national stage application of International Application No. PCT/EP2010/002740, filed May 5, 2010, which claims priority to EP 09006673, filed May 18, 2009, the entire disclosures of which are hereby incorporated by reference.

BACKGROUND

The present invention relates to an adaptor with a first connection for a nebuliser and a second connection on the patient side an inhalation device having a chamber for the intermediate storage of an aerosol, having a first port for connection with a nebuliser that produces the aerosol and a second port on the patient side for delivering the aerosol and with a third port for breathable air and a nebuliser, particularly an inhaler, having such an adaptor or an inhalation device of this kind.

Nebulisers, particularly inhalers, serve to supply a user or patient with an aerosol, i.e. a nebulised fluid, which preferably comprises or contains a medicament or constitutes a medicament preparation. During administration, very precise dosing is often desirable or essential. It is therefore important that a dose dispensed in aerosol form by a nebuliser should be inhaled as completely as possible.

A starting point of the present invention is a nebuliser as described in principle in WO 91/14468 A1 and specifically in WO 97/12687 A1 (FIGS. 6a, 6b). The known nebuliser comprises a pressure generator for conveying and nebulising a medicament preparation. The medicament preparation is delivered in aerosol form through a mouthpiece.

A problem with nebulisers in general is that the triggering of the nebulisation and breathing in have to be co-ordinated. This may be difficult for individual users.

WO 2004/091704 A1 discloses an inhalation device for the intermediate storage of a generated aerosol in a chamber. The known inhalation device is provided for an MDI (Metered Dose Inhaler) and serves to slow down the aerosol, particularly by lengthening the flow path. For this reason, inhalation devices of this kind are also known as spacers. Moreover, the inhalation device serves to store the aerosol produced intermediately so that the user has sufficient time to inhaler the aerosol.

Respiration equipment and systems are used to supply a patient with a breathable gas, generally through at least one gas-carrying tube. In ventilated patients as well, treatment by inhalation may be provided in which an aerosol generated by a nebuliser is introduced into the breathable gas or is breathed-in or inhaled with the breathable gas.

WO 2007/141201 A1 discloses an adaptor having a first connection for a nebuliser and a second connection at the patient end. The known adaptor has a third connection for a breathing tube for supplying a breathing gas. The adaptor is thus designed for connection to a ventilator or ventilating tube. The breathable air supplied through it is conveyed to the first connection of the adaptor and there it is diverted alongside a nozzle of the associated nebuliser protruding into the second connection of the adaptor and together with the aerosol generated by the nebuliser it is expelled through the second connection.

SUMMARY

The aim of the present invention is to provide a simple and/or universally useable adaptor for a nebuliser, an improved inhalation device having a chamber for the intermediate storage of an aerosol produced by a nebuliser, and a nebuliser comprising such an adaptor and/or an inhalation device of this kind.

According to a first aspect of the present invention, an adaptor is provided which has a first connection with an oval cross-section for connecting to an oval mouthpiece of a nebuliser. This provides a very simple means of connection to the associated nebuliser or its mouthpiece.

According to a second aspect of the present invention, an adaptor is provided which comprises a first connection having a connector for accommodating a nozzle of the nebuliser. This is a very simple means of ensuring a good fluidic connection to the associated nebuliser.

According to a third aspect of the present invention an adaptor is provided in which the first connection for the nebuliser and a second connection at the patient end are joined together with no diversions. In particular, the second connection is embodied for connecting to a tube or an inhalation device. This allows for a particularly simple construction and permits particularly universal use of the associated nebuliser together with the adaptor, particularly for attaching to restoration systems or the like. In view of its very simple structure the adaptor is preferably used as a disposable item or is used only once.

According to a fourth aspect of the present invention an inhalation device is provided having a chamber for intermediate storage of an aerosol, wherein the chamber is fluidically connected in valve-free manner on the inlet side to a first port for a nebuliser—at least when the nebuliser is attached—and is connected in parallel on the inlet side via an inlet valve to a port for supplying breathable air, so that breathable air can flow from the latter port through the inlet valve into the chamber. This allows in particular unimpeded or substantially loss-free inflow of aerosol into the chamber, so that the undesirable settling of nebulised fluid on a valve on the inlet side of the chamber can be avoided.

In particular, the chamber is also attached on the outlet side, in valve-free manner, to a patient-side port, so that the aerosol can flow out through the patient-side port largely unimpeded and without loss as it is removed from the chamber.

According to a fifth aspect of the present invention an inhalation device is provided having a chamber for the intermediate storage of aerosol, wherein the chamber comprises on the outlet side a plurality of outlet openings arranged at least substantially in a ring. This surprisingly allows relatively loss-free outflow of the aerosol from the chamber.

According to a sixth aspect of the present invention the adaptor is connected or connectable, more particularly in releasable manner, to an inhalation device having a chamber for the intermediate storage of aerosol. This makes it possible to produce a modular system of simple construction which can be used in highly universal manner. If necessary, the adaptor may also be exchanged or used only once, whereas the inhalation device can be used repeatedly, if necessary.

According to a seventh aspect of the present invention a nebuliser is provided in conjunction with an adaptor as mentioned above and/or an inhalation device as mentioned above. This allows particularly universal use of the nebuliser, particularly also in ventilated patients or in conjunction with ventilating equipment or systems.

The above-mentioned aspects of the present invention and the features and aspects of the invention that are apparent from the further description and claims may be implemented independently of one another and in any desired combinations.

Further advantages, features, properties and aspects of the present invention will become apparent from the claims and the following description of a preferred embodiment by reference to the drawings, wherein:

BRIEF DESCRIPTION OF THE DRAWING

FIG. 14 is a schematic section through the inhalation device during breathing in; and FIG. 15 is a schematic section through a proposed inhalation device according to a third embodiment during breathing in.

DESCRIPTION OF EMBODIMENTS

Figure 1:
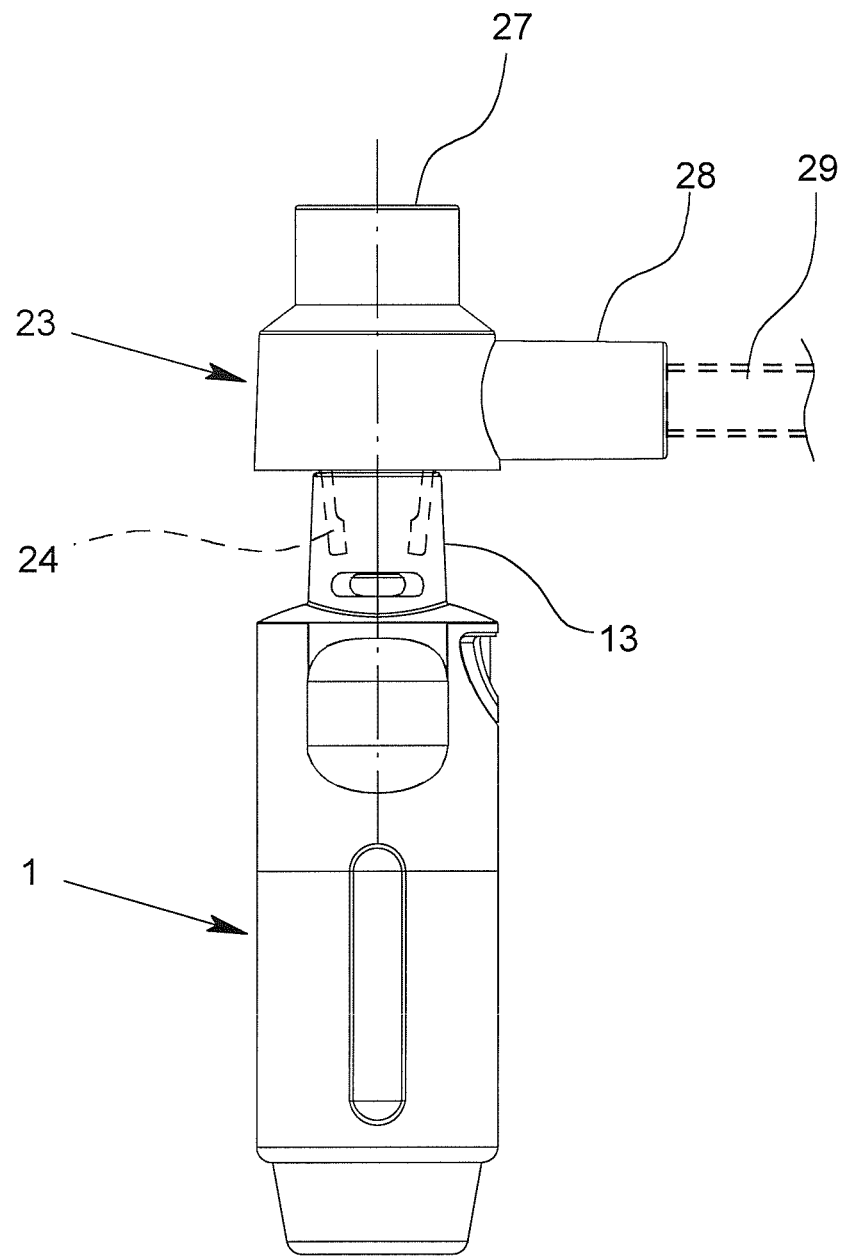
FIG. 1 is a schematic view of a proposed adaptor according to a first embodiment having a nebuliser attached thereto.

In the figures, the same reference numerals have been used for identical or similar parts where corresponding or comparable properties and advantages are achieved, even if the relevant description has not been repeated.

FIG. 1 is a schematic view of a proposed adaptor 23 having an associated nebuliser 1 attached thereto in the drawing.

Figure 2:
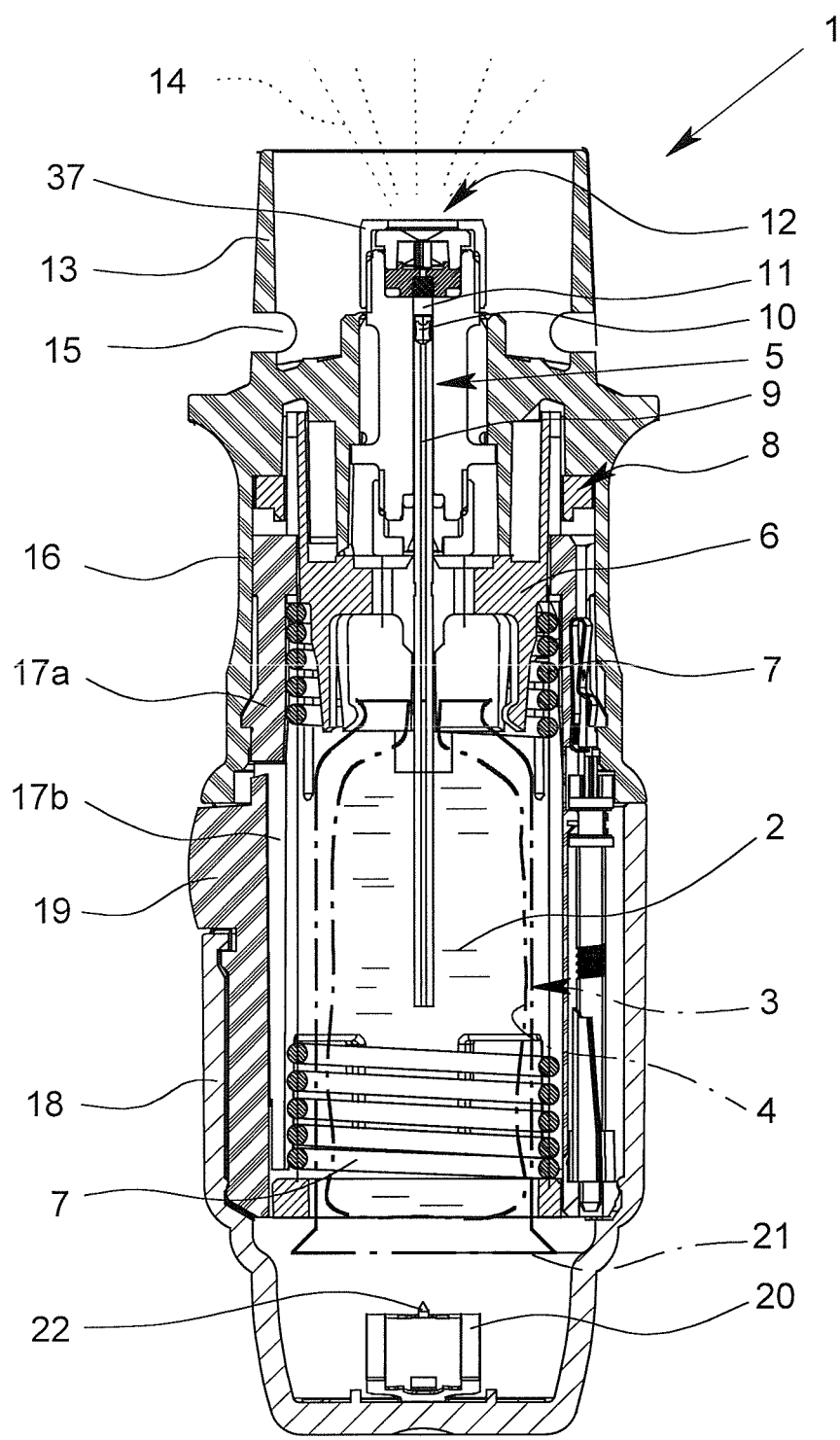
FIG. 2 is a schematic section through a nebuliser in the untensioned state.
Figure 3:
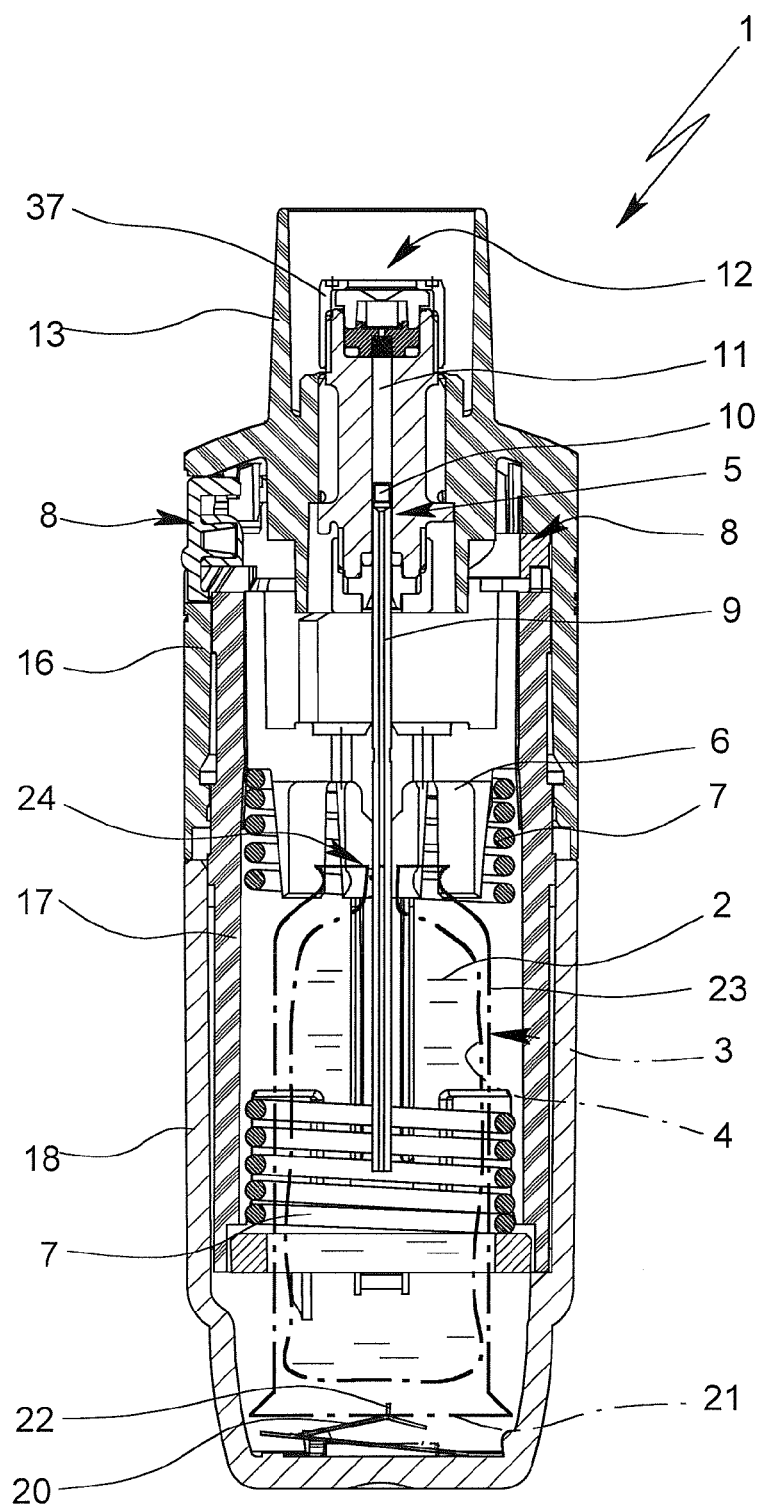
FIG. 3 is a schematic section, rotated through 90° compared with FIG. 2, through the nebuliser in the tensioned state.

FIGS. 2 and 3 show the preferably portable nebuliser 1 for the propellant free nebulisation of a fluid, preferably a liquid or medicament preparation 2 in a schematic view in the untensioned state (FIG. 2) and in the tensioned state (FIG. 3). FIGS. 2 and 3 show the nebuliser 1 with a container 3 holding the medicament preparation 2.

During the nebulisation of the medicament preparation 2, preferably a liquid, a respirable aerosol 14 (FIG. 2) is formed which can be breathed-in or inhaled by a user or patient (not shown). Normally, inhalation takes place at least once a day, but particularly several times a day, preferably at specified intervals of time, more particularly depending on the complaint suffered by the patient.

The nebuliser 1 comprises the preferably insertable and optionally exchangeable container 3 holding the medicament preparation 2. The container 3 thus forms a reservoir for the medicament preparation 2 which is to be nebulised. Preferably, the container 3 contains a sufficient quantity of medicament preparation 2 or active substance for several doses of the medicament preparation 2, in order to allow a number of nebulisations or applications. A typical container 3 as disclosed in WO 96/06011 A1 holds a volume of about 2 to 10 ml. With regard to the preferred construction of the container 3 reference is additionally made to WO 00/49988 A2.

The container 3 is preferably substantially cylindrical or cartridge-shaped and can be inserted into the nebuliser 1 from below, after it has been opened, and optionally exchanged. It is preferably of rigid construction, the medicament preparation 2 being contained in particular in a collapsible bag 4 in the container 3.

The nebuliser 1 also comprises a conveying device, particularly a pressure generator 5, for conveying and nebulising the medicament preparation 2, particularly in a predetermined and optionally adjustable dosage amount in each case.

The nebuliser 1 or pressure generator 5 comprises in particular a holder 6 for the container 3 and associated drive spring 7 which is only partly shown, preferably having an associated locking element 8 which is manually operable to release it, a conveying element, preferably a conveying tube 9 in the form of a capillary, with an optional valve, particularly a non-return valve 10, a pressure chamber 11 and/or a delivery nozzle 12, particularly in the region of a mouthpiece 13.

The container 3 is fixed in the nebuliser 1 by means of the holder 6, particularly by a clamping or latching action, such that the conveying tube 9 protrudes into the container 3. The holder 6 may be constructed such that the container 3 can be exchanged.

When the drive spring 7 is axially tensioned, the holder 6 with the container 3 and the conveying tube 9 is moved downwards in the figures and the medicament preparation 2—or more precisely the next dose—is sucked out of the container 3 into the pressure chamber 11 of the pressure generator 5 through the non-return valve 10.

During the subsequent release of tension after actuation of the locking element 8, the medicament preparation 2 in the pressure chamber 11 is placed under pressure by moving the conveying tube 9 back up, with the non-return valve 10 now closed, by releasing the tension on the drive spring 7, so that this conveying tube 9 now acts as a pressure ram. This pressure expels the medicament preparation 2 through the delivery nozzle 12, where it is nebulised into the preferably respirable aerosol 14, as shown in FIG. 2.

The user or patient (not shown) can inhale the aerosol 14, while preferably supply air can be sucked into the mouthpiece 13 through at least one supply air opening 15.

During the nebulisation process the container 3 is moved back into its original position by the drive spring 7. The container 3 thus performs a lifting movement during the tensioning process and during the nebulisation process.

The nebuliser 1 comprises in particular a first housing part (upper part) 16 and an inner part 17 which is rotatable relative thereto (FIG. 3) having an upper part 17a and a lower part 17b (FIG. 2), while a second housing part (lower part) 18, which is in particular manually operable or rotatable, is releasably attached, in particular pushed onto the inner part 17, preferably by means of a safety closure or retaining element 19. In particular, the safety closure or retaining element 19 is constructed such that accidental opening of the nebuliser 1 or removal of the second housing part 18 is prevented. In particular, in order to release the second housing part 18, the retaining element 19 has to be pressed in against spring force. In order to insert and/or replace the container 3 the second housing part 18 can be detached from the nebuliser 1. The second housing part 18 preferably forms a cap-like lower housing part and/or engages around or over a lower free end portion of the container 3.

The second housing part 18 can be rotated relative to the first housing part 16, whereby the inner part 17 is also rotated. In this way the drive spring 7 is tensioned in the axial direction by means of a gear (not shown in detail) acting on the holder 6. During tensioning the container 3 is moved axially downwards or with its end portion (further) into the second housing part 18 or towards the end face thereof, until the container 3 assumes an end position shown in FIG. 3. In this state the drive spring 7 or nebuliser 1 is clamped and locked.

The nebuliser 1 preferably has a device for forcibly ventilating the container 3.

When tensioning first takes place, the container 3 is preferably pierced in its base or opened. In particular, an axially acting spring 20 arranged in the housing part 18 comes to abut on the container base 21 and with a piercing element 22 pierces the container 3 or an in particular gas tight seal provided in the base for ventilation purposes when contact is first made.

The device for forcible ventilation is thus formed in this case by the piercing element 22, which is held or formed by the spring 20. However, other design solutions are also possible.

It should be noted that during the piercing for ventilation purposes only the outer shell of the container 3 is opened. The bag 4 containing the medicament preparation 2 remains undamaged. As the medicament formulation 2 is removed from the bag 4 through the conveying tube 9 the flexible bag 4 collapses. For pressure equalisation, ambient air can flow into the container 3 through the ventilation or piercing opening.

In order to use the nebuliser 1, first of all the container 3 has to be inserted. This is preferably done by removing or pulling out the second housing part 18. The container 3 is then axially inserted or pushed into the inner part 17. At the same time the container 3 is opened at the head end or attached. This is done by means of the conveying element, i.e. the conveying tube 9, which pierces a seal preferably provided at the head end of the container 3 and is then inserted through a septum at the head end of the container 3 into the interior of the bag 4. Thus the fluidic connection between the container 3 or more accurately between the bag 4 in the container 3 via the conveying tube 9 to the pressure generator 5 or pressure chamber 11 is produced.

Then the second housing part 18 is pushed on again. The nebuliser 1 can now be tensioned for the first time. At this stage the container 3 is then pierced at its base by the piercing element 22, i.e. forcibly ventilated, as explained previously.

Before being used for the first time and after the container 3 has been inserted and fluidically connected, the nebuliser 1 is preferably tensioned and actuated several times. This so-called priming displaces any air present in the medicament preparation 2 in the conveying tube 9 and in the pressure generator 5 to the delivery nozzle 12. The nebuliser 1 is then ready for inhalation.

The quantity of medicament preparation 2 delivered per spray or nebulisation process is preferably about 10 µl to 50 µl, more particularly about 10 µl to 20 µl, most preferably about 15 µl.

The drive spring 7 is preferably installed in a biased state in order to achieve a high spring pressure. In the proposed nebuliser 1 the pressurisation and conveying of the medicament preparation 2 during the nebulisation process namely takes place preferably only by spring force, and more particularly only by the force of the drive spring 7.

The nebuliser 1 is preferably constructed such that the medicament preparation 2 in the pressure generator 5 or in the pressure chamber 11 reaches a pressure of 5 MPa to 60 MPa, particularly about 10 MPa to 50 MPa during delivery. Particularly preferably, during the delivery or nebulisation of the medicament preparation 2, a pressure of about 5 MPa to 60 MPa, more particularly about 10 to 30 MPa, is reached at the delivery nozzle 12 or at the nozzle openings thereof. The medicament preparation 2 is then converted into the aerosol 14, the droplets of which have an aerodynamic diameter of up to 20 µm, preferably about 3 µm to 10 µm. The nebulising activity or nebulising effect is achieved or further assisted by preferably intercepting jets delivered by the delivery nozzle 12.

The nebuliser 1 is preferably constructed such that the aerosol 14 is delivered at low speed, particularly at a speed of less than 2 m/s, most preferably about 1.6 m/s or less (in each case measured at a distance of 10 cm from the delivery nozzle 12). The nebuliser 1 is thus preferably in the form of a so-called soft mist inhaler. The low delivery speed can be obtained or assisted by intercepting jets of the medicament preparation 2, which are delivered by the delivery nozzle 12 and/or by a suitable choice of spring force.

Particularly preferably, the construction of the nebuliser 1 is such that the aerosol generation lasts for at least 1 s and in particular at least 1.5 s. The time taken to nebulise a dose or to actuate the nebuliser 1 is thus at least 1 s, more particularly more than 1.5 s.

Figure 4:
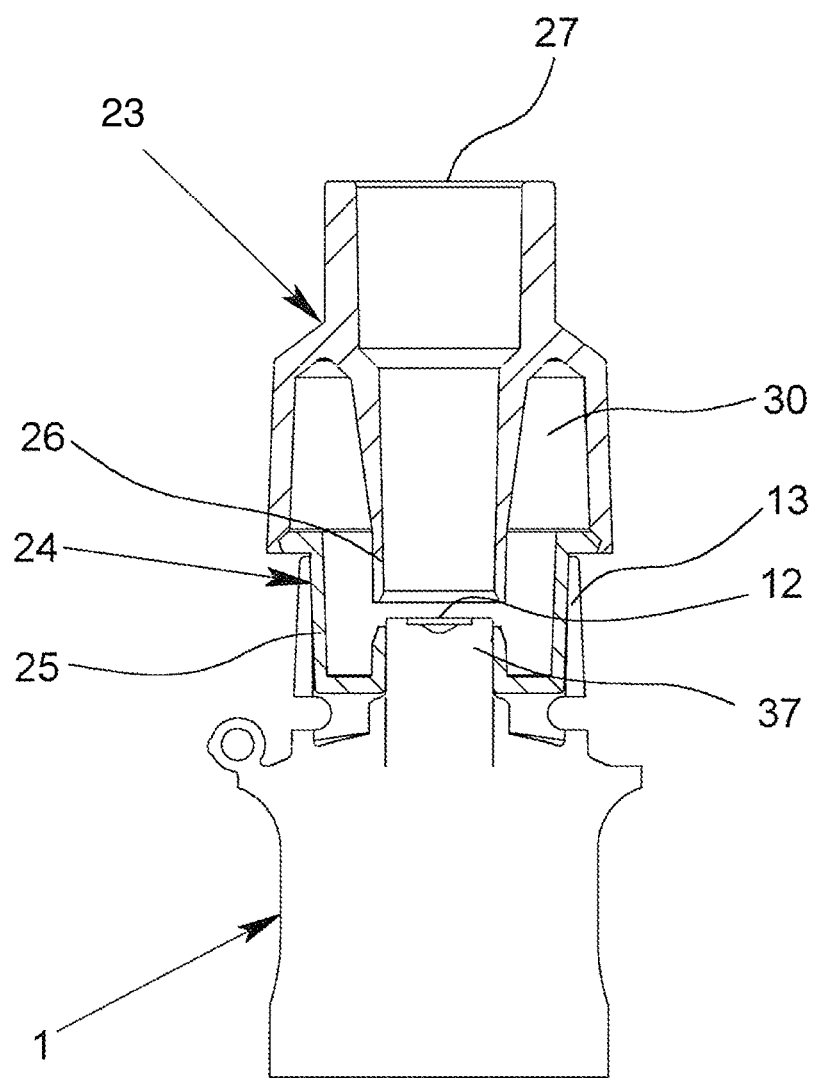
FIG. 4 is a schematic section through the nebuliser with the adaptor attached.

FIG. 4 shows, in schematic section, the adaptor 23 and parts of the attached nebuliser 1, which are shown only schematically.

The adaptor 23 is preferably connected or connectible to the nebuliser 1 or its mouthpiece 13 in releasable and/or more particularly clamping or latching manner.

The adaptor 23 comprises a first connection 24 for the nebuliser 1, more accurately for fluidic and preferably also mechanical connection to the nebuliser 1 or its mouthpiece 13.

In the embodiment shown, the first connection 24 preferably comprises a connecting portion 25 which extends into the mouthpiece 13 and more particularly can be inserted therein. The connecting portion 25 is accordingly adapted in its outer contour to the inner contour of the mouthpiece 13. For example, on its outside, the connecting portion 25 tapers towards the free end and is thus embodied to the at least substantially complementary to a preferably slightly conical shape of the mouthpiece 13. However, other design solutions are also possible.

In the embodiment shown, the first connection 24 or its connecting portion 25 preferably has an oval cross-section for connecting to the preferably oval mouthpiece 13 of the nebuliser 1.

In the embodiment shown the connecting portion 25 preferably closes off a) the substantially annular intermediate space between the expulsion nozzle 12 projecting into the mouthpiece 13 and the inner wall of the mouthpiece 13 with a holder or a projection 37, and/or b) directly closes off the air supply openings 15, particularly so that supply air flows in through the supply air opening or openings 15 only to a lesser extent or not at all into the mouthpiece 13 when the nebuliser 1 or adaptor 23 is used.

The adaptor 23 preferably comprises a connector 26 or other particularly channel-like portion which, when the nebuliser 1 is attached, is associated with the expulsion nozzle 12, particularly covers or receives it or is arranged adjacent thereto, in order to receive or convey onwards the aerosol 14 dispensed by the nebuliser 1 or the expulsion nozzle 12.

In the embodiment shown, the connector 26 terminates at an axial spacing from the expulsion nozzle 12 or a holder associated with the expulsion nozzle 12, so that supply air or breathable air from a ventilation apparatus can flow into the connector 26 (laterally) with the aerosol 14 or flow past the expulsion nozzle 12.

However, it is theoretically also possible for the first connection 24 or connector 26 to be connectible (at least substantially) in leak-tight manner to the expulsion nozzle 12 or a projection 37 that holds or surrounds the expulsion nozzle 12, particularly preferably by fitting on the connector 26, so that no supply air or breathable air can flow past the expulsion nozzle 12 through or into the first connection 24.

The adaptor 23 has a second connection 27 at the patient end. The second connection 27 is preferably in the form of a tube or bore and/or comprises in particular an at least substantially round cross-section.

The second connection 27 is preferably configured for mechanical and/or fluidic connection to a tube, a ventilation apparatus or an inhalation device. However, the second connection 27 may also theoretically be in the form of a mouthpiece.

In the embodiment shown, the adaptor 23 preferably has a third connection 28 shown only in FIG. 1 for supply air or breathable air. The third connection 28 is preferably configured for mechanical and/or fluidic connection to a ventilating tube 29, indicated only by dashed lines, or some other ventilation equipment or the like. For this purpose the third connection 28 is preferably embodied as a connection, tube or pipe, and/or such that the tube 29 or the like can preferably inserted or fitted on.

The present invention preferably relates to use in a ventilated patient or with a ventilator. Accordingly, the term breathable air is generally used hereinafter. The term "breathable air" is preferably to be understood as being a ventilating gas which is provided by a ventilating apparatus or ventilating system for ventilating a patient. Theoretically, the breathable air may also be other supply air and/or exhaled air, particularly when the direction of flow is reversed. The term "breathable air" is therefore preferably to be understood very broadly, so as to cover these alternatives.

The third connection 28 is preferably formed by the adaptor 23 or moulded onto it.

Through the third connection 28, breathable air can preferably be supplied to the first connection 24 or second connection 27 via an annular channel 30 formed by or in the adaptor 23, so that the breathable air can be mixed with the aerosol 14 and/or expelled together with the aerosol 14 through the second connection 27.

In the embodiment shown, the breathable air preferably forms an enveloping current for the aerosol 14 emitted from the expulsion nozzle 12. This is preferably achieved here by guiding the breathable air at least substantially in an annular shape and/or with a twist in the region of the expulsion nozzle 12 and then enabling it to flow through the first connection 24 or connector 26, together with the aerosol 14 (which is not shown in FIG. 4) to the second connection 27. A corresponding fluidic connection is formed for this purpose in the adaptor 23.

The aerosol 14 and the breathable air can then be delivered to the patient (not shown) through the second connection 27, for example by means of a ventilation tube attached thereto, using a face mask or the like.

It should be noted that the third connection 28 is purely optional. Instead of the third connection 28, supply air or breathable air can alternatively be supplied through the supply air opening or openings 15 of the nebuliser 1 or the like.

Further preferred embodiments are explained hereinafter. The previous remarks and explanations apply in a supplementary capacity, in particular, even if the description has not been repeated.

Figure 5:
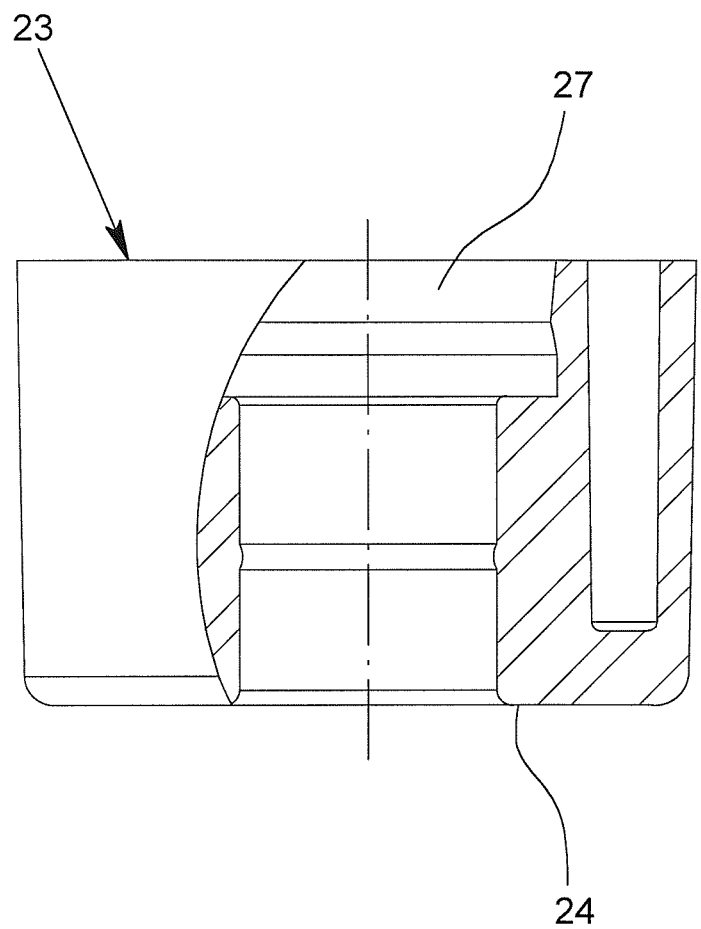
FIG. 5 is a schematic section through a proposed adaptor according to a second embodiment.

FIG. 5 shows in schematic section a second embodiment of the proposed adaptor 23.

The adaptor 23 is preferably embodied as a disposable item or intended for single use. This makes economic sense because of the particularly simple structure of the adaptor 23 according to the second embodiment, as there is then no need to clean and more particularly sterilise the adaptor 23 after each use.

In the second embodiment the first connection 24 is fluidically connected to the second connection 27 without any branches and more particularly in one piece. In particular, the adaptor 23 does not have a third connection 28. Thus there is no supply of breathable air or supply air at least on the adaptor side.

Figure 6:
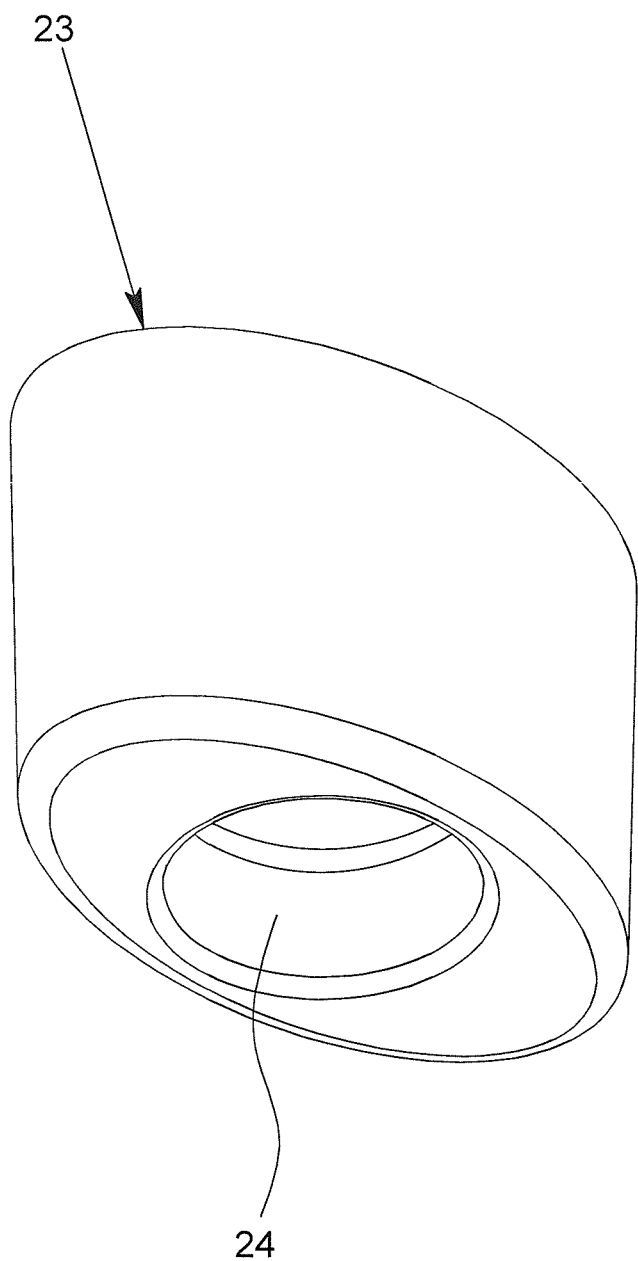
FIG. 6 is a perspective view of the adaptor according to FIG. 5.
Figure 7:
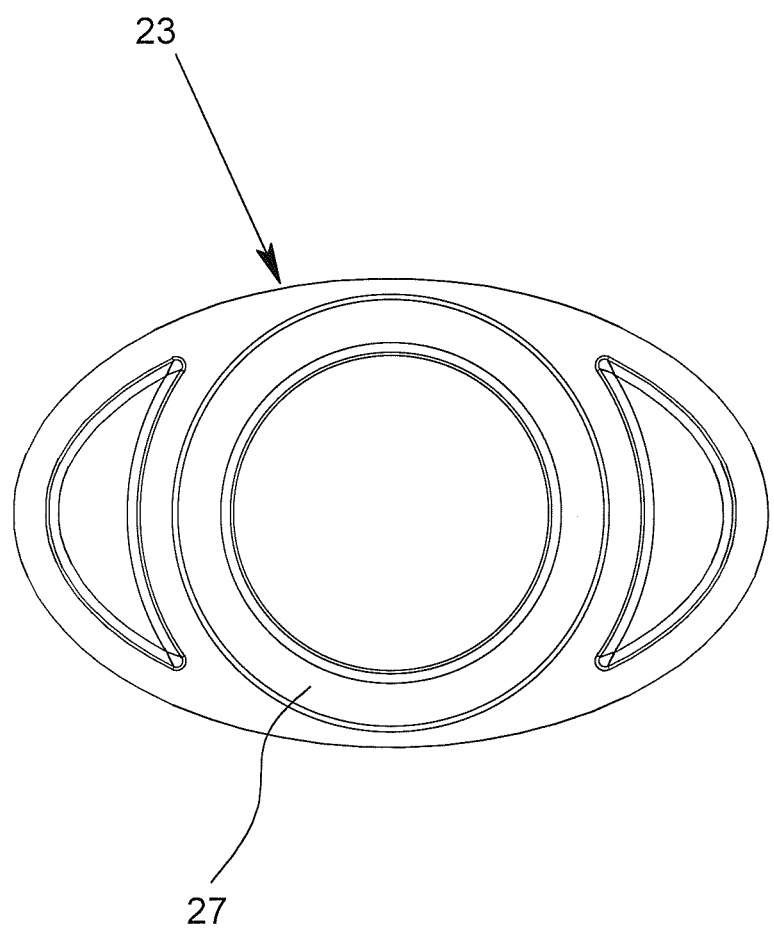
FIG. 7 is a plan view of the adaptor according to FIG. 5.

Preferably, the first connection 24 or the adaptor 23 itself has an oval cross-section, in this case an oval outer contour, for connection to the preferably oval mouthpiece 13 of the nebuliser 1, in this case by insertion in the mouthpiece 13. The preferred oval shape is shown in the perspective view according to FIG. 6 and the plan view according to FIG. 7.

The adaptor 23 is preferably constructed in one piece.

Preferably, the adaptor 23 is embodied as an injection moulded component and/or made of plastics.

In the second embodiment the first and second connections 24, 27 are joined together at least substantially by a preferably straight bore. The first connection 24 comprises a preferably hollow cylindrical inner contour for accommodating the expulsion nozzle 12 or the aerosol 14 emitted therefrom. Particularly preferably, a projection 37 of the nebuliser, which holds or surrounds the expulsion nozzle 12 and is particularly cylindrical, can be inserted in the first connection 24. Thus the expulsion nozzle 12 can be connected in substantially gas-tight manner to the first connection 24. In this case, no supply air can flow through the supply air openings 15 into the first connection 24.

However, it is theoretically also possible for supply air to flow through at least one supply air opening 15 of the nebuliser 1 or the like into the first connection 24 and together with the aerosol 14 to the second connection 27.

The second connection 27 (at the patient end) is preferably embodied as a bushing and/or undercut, so as to be connectable particularly by a latching and/or clamping action to a tube, an inhalation device, a mouthpiece, a face mask or the like. However, other design solutions are also possible.

Figure 8:
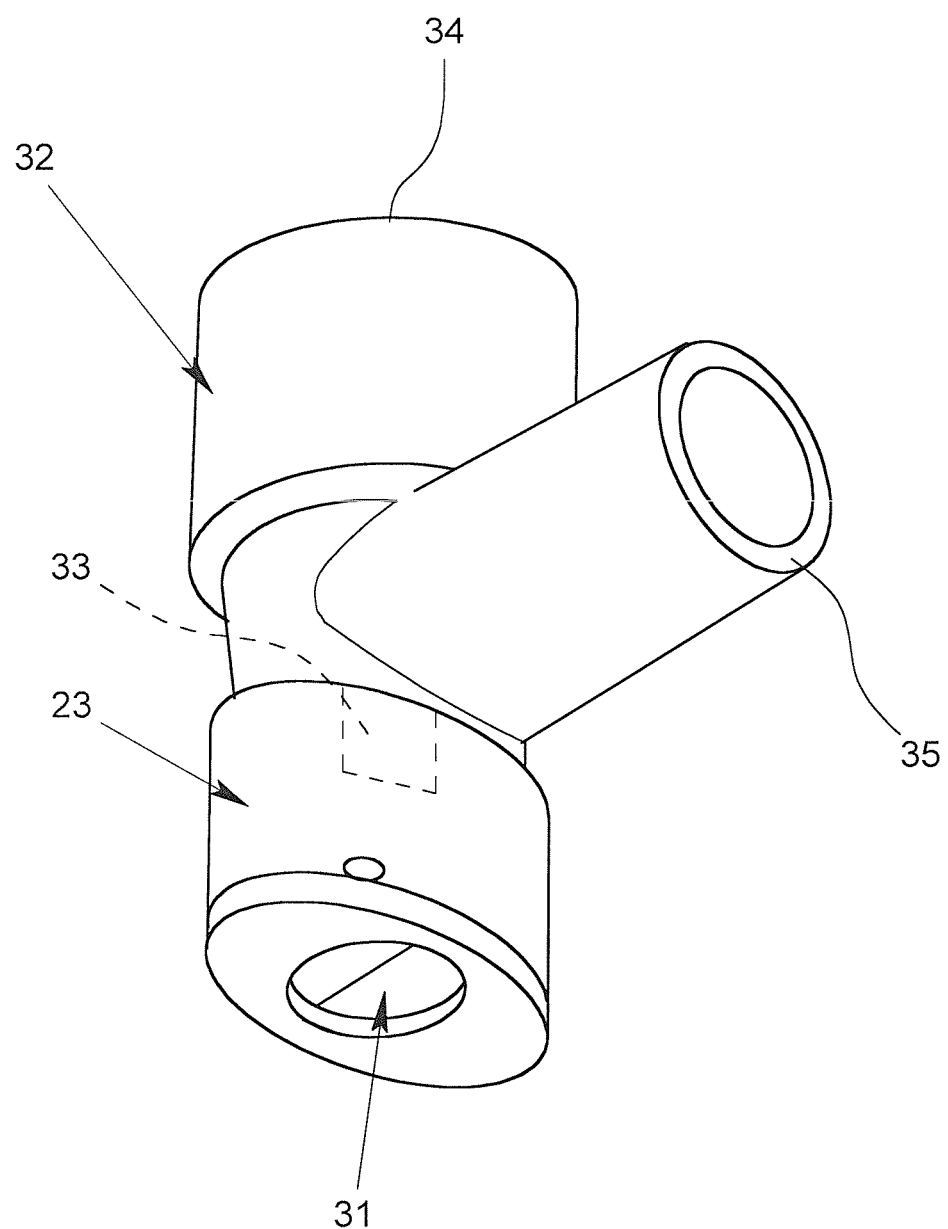
FIG. 8 is a perspective view of a proposed adaptor according to a third embodiment with an attached inhalation device according to a first embodiment.

FIG. 8 shows in perspective view the proposed adaptor 23 according to a third embodiment.

Figure 9:
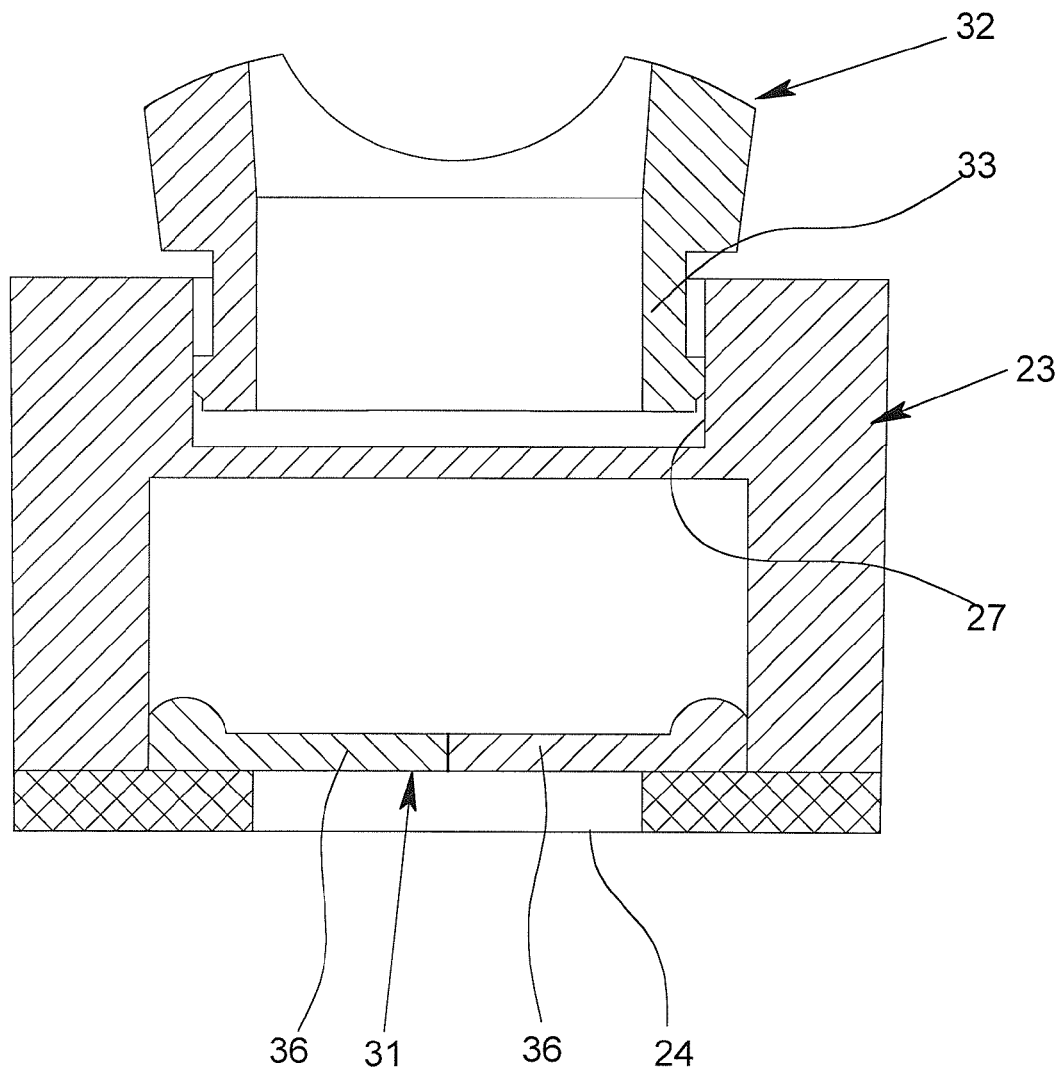
FIG. 9 is sectional representation of an adaptor according to FIG. 8 with no nebuliser attached.
Figure 10:
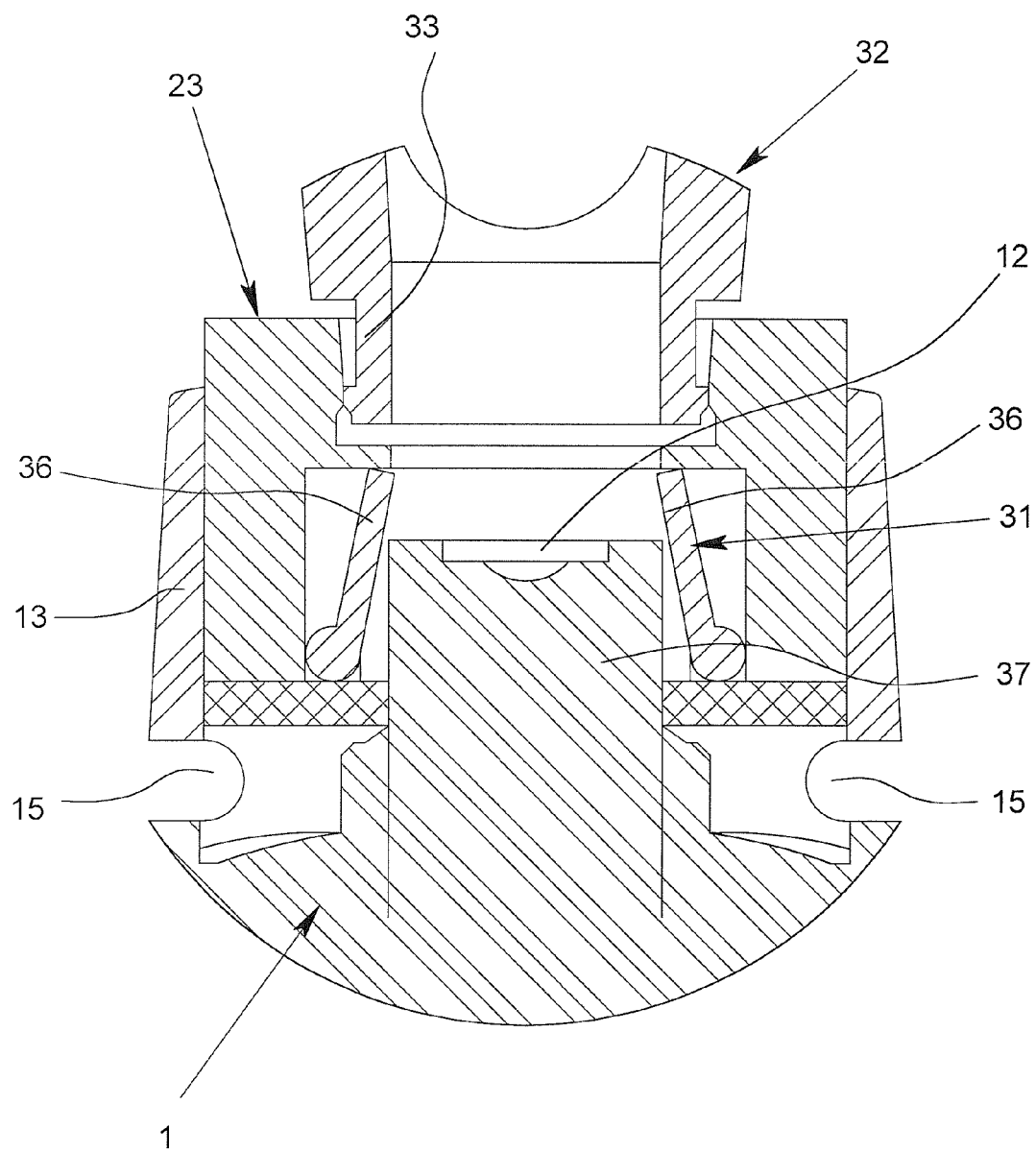
FIG. 10 is a sectional representation of an adaptor according to FIG. 8 with the nebuliser attached.

In the third embodiment the adaptor 23 comprises a locking valve 31 which is necessarily open when the adaptor 23 is connected to the nebuliser 1 and is closed when the adaptor 23 is separated from the nebuliser 1. FIG. 9 shows in schematic section the adaptor 23 when the locking valve 31 is closed, i.e. in the state where it is separated from the nebuliser 1. FIG. 10 shows in schematic section the adaptor 23 with the locking valve 31 open, namely in the state in which it is connected to the nebuliser 1.

FIG. 8 shows the adaptor 23 with an inhalation device 32 attached on the outlet side, i.e. to the second connection 27, this device forming an angled piece, in particular.

FIG. 9 shows in schematic section a part of the inhalation device 32, specifically a first port 33 for the nebuliser 1, which can be attached directly via the adaptor 23. Accordingly, the adaptor 23 is connected or connectable by its second connection 27 to the first port 33 of the inhalation device 32, particularly mechanically and/or fluidically. In the embodiment shown the connection 27 and port 33 are connected to one another in particular by a latching or clamping action, in this case by the insertion of the port 33 into the connection 27.

In the embodiment shown the inhalation device 32 is not directly connected to the nebuliser 1 but is connected indirectly via the adaptor 23. This is a preferred embodiment. In particular, the adaptor 23 may be replaceable, particularly preferably if it is releasably connected or connectable to the inhalation device 32.

The inhalation device 32 preferably comprises a second port 34 on the patient side for dispensing breathable air and aerosol 14 (not shown) preferably mixed in via the adaptor 23.

The inhalation device 32 preferably comprises a third port 35 for supplying breathable air, particularly for connection to a tube, not shown here, of a ventilation apparatus or the like (not shown).

The schematic section according to FIG. 10 additionally schematically shows a part of the attached nebuliser 1. In the embodiment shown the locking valve 31 comprises at least one, and in this case two, movable valve elements 36 which are opened in particular by the expulsion nozzle 12 or the projection 37 of the nebuliser 1 that holds the expulsion nozzle 12. However, other design solutions are also possible.

The locking valve 31 is preferably biased into the closed position and/or is configured to be self-closing, particularly by means of at least one restoring means (not shown) such as a spring or the like.

When the nebuliser 1 is used, the aerosol 14 produced by the nebuliser 1 is dispensed through the adaptor 23, in this case to the inhalation device 32. From there, the aerosol 14 can be supplied, in particular together with breathable air, to a patient (not shown) who is being ventilated, in particular. The ventilation is carried out in particular by a corresponding supply of breathable air.

Additional embodiments of the inhalation device 32 are explained hereinafter. The remarks and explanations given previously apply particularly in a supplementary manner, even if the relevant description is not repeated.

Figure 11:
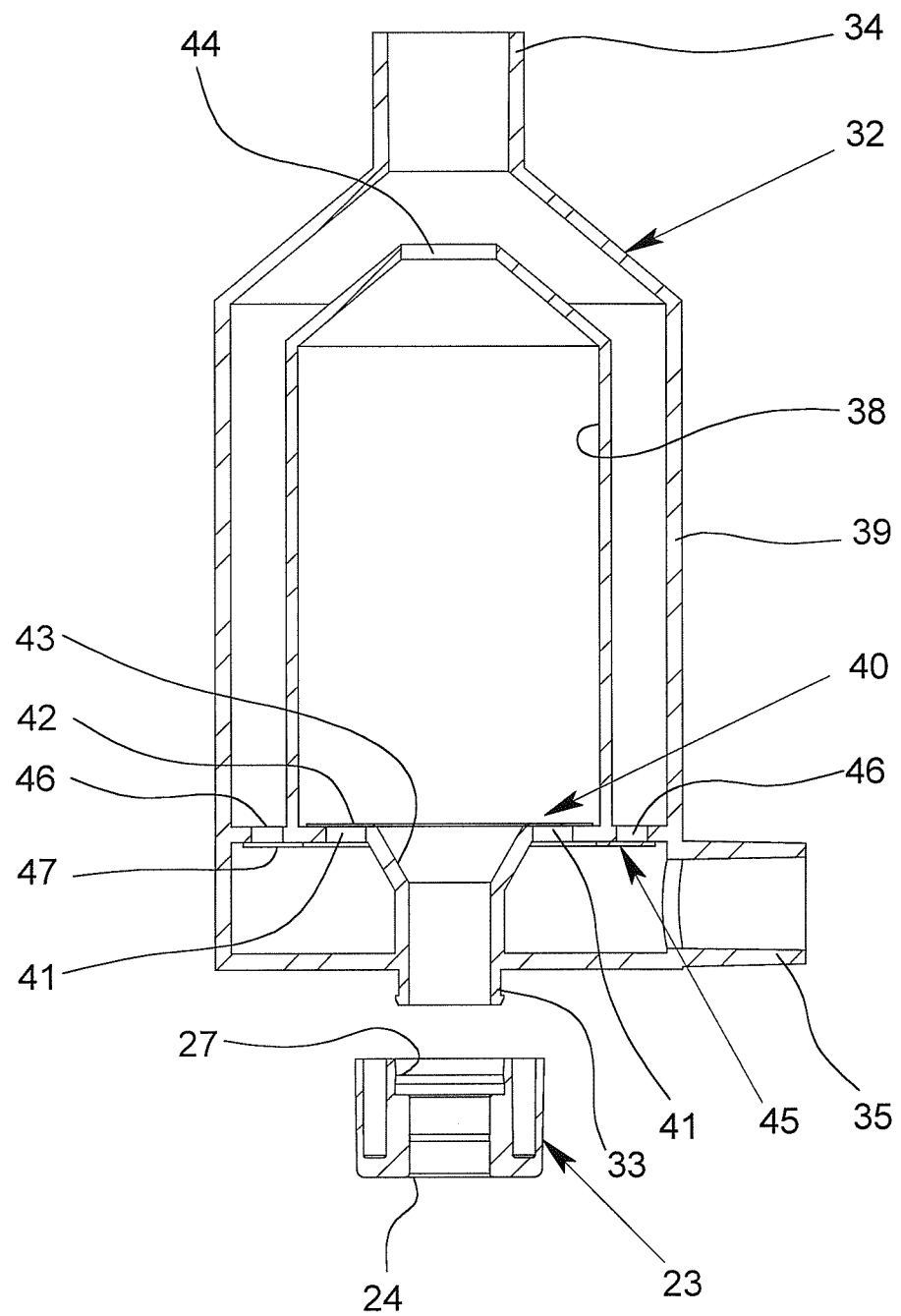
FIG. 11 is a schematic section through a proposed inhalation device according to a second embodiment with an associated adaptor.

FIG. 11 is a schematic sectional representation of the proposed inhalation device 32 according to a second embodiment.

As in the previous embodiment the inhalation device 32 may be attached to the nebuliser 1 via the adaptor 23. However, the first port 33 of the inhalation device 32 may also be configured for direct connection to the nebuliser 1 or mouthpiece 13. If desired, the adaptor 23 or the optional locking valve 31 thereof may also be integrated in the inhalation device 32 or its port 33. In particular, the first port 33 of the inhalation device 32 is then configured for fluidic and/or mechanical connection to the nebuliser 1 or its mouthpiece 13.

The inhalation device 32 preferably comprises a chamber 38 for the intermediate storage of the aerosol 14 (not shown) produced by the nebuliser 1. In particular, this is an inner chamber which is arranged within a housing 39 of the inhalation device 32.

The chamber 38 is fluidically connected to the first port 33 preferably directly, more particularly without a valve, especially so that at least when the nebuliser 1 is attached the aerosol 14 produced by the nebuliser 1 can flow into the chamber 38 in valve-free and if possible without any wastage. If the locking valve 31 is provided, this is open when the nebuliser 1 is attached and thus does not constitute a valve that has to be opened by the aerosol 14, or an obstacle to be overcome.

By the term "free from wastage" is meant in particular, in the present invention, that unwanted precipitation of the aerosol 14 or of the nebulised fluid is substantially prevented or at least minimised.

The chamber 38 is connected on the inlet side not only to the first port 33 but preferably in parallel on the inlet side to the third port 35 of the inhalation device 32, via an inlet valve 40, so that breathable air can flow from the third port 35 into the chamber 38 or through the chamber 38, particularly at least substantially parallel to the main direction of the flow of the aerosol 14.

Figure 12:
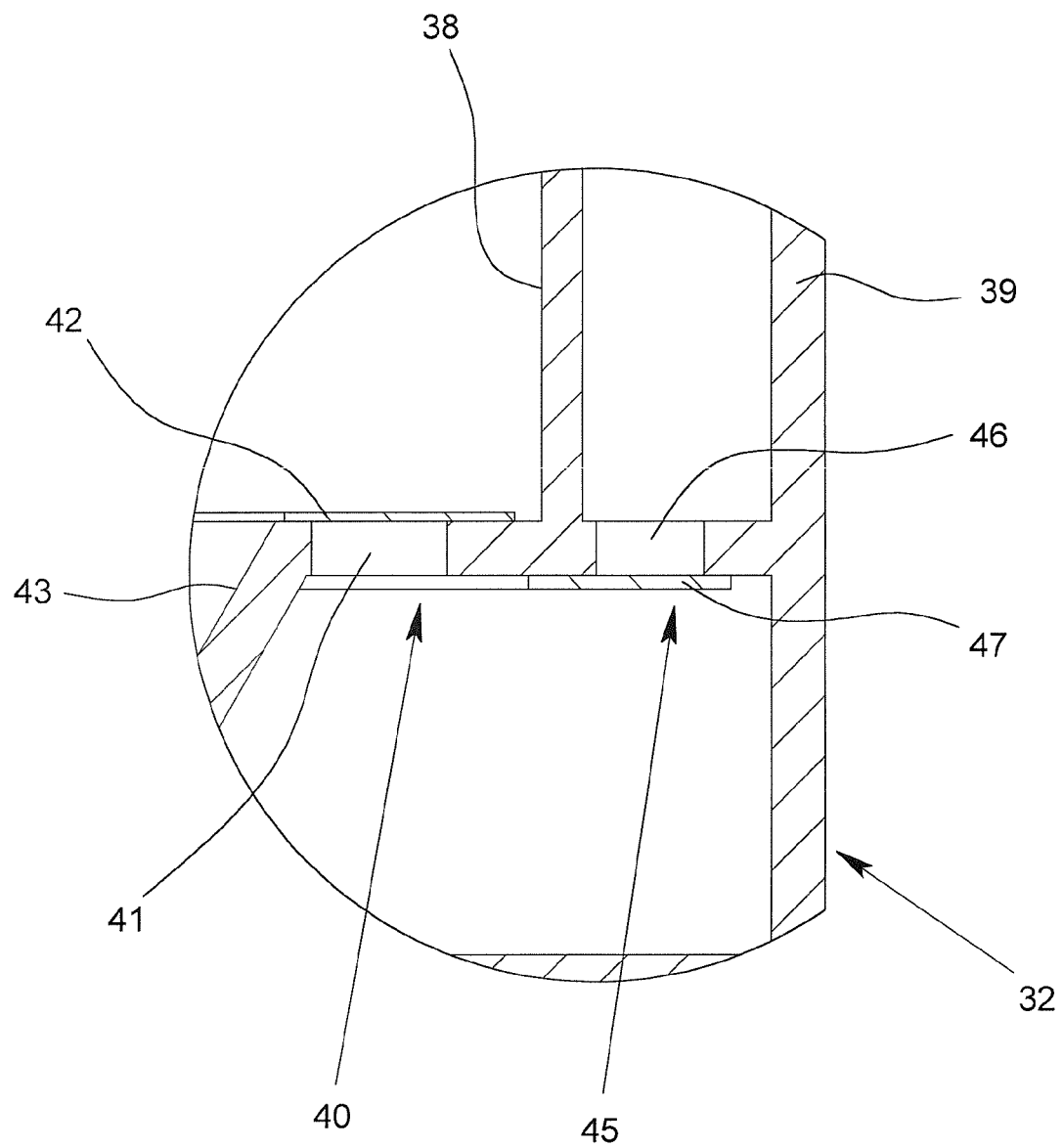
FIG. 12 is a magnification of a detail from FIG. 11.

The inlet valve 40 is schematically shown in FIG. 11 and in the detailed magnification of FIG. 11 shown in FIG. 12. In particular, it is a one-way or non-return valve. The inlet valve 40 is preferably configured to be self-closing and/or (slightly) biased into the closed position.

In the embodiment shown, the inlet valve 40 preferably comprises a plurality of inlet openings 41 which can be covered or closed off in particular by a common valve element 42, or a plurality of separate valve elements 42.

The inlet openings 41 are preferably arranged about a central or middle connecting channel 43 which connects the first port 33 to the chamber 38. However, other design solutions or arrangements are also possible.

On the outlet side the chamber 38 is preferably fluidically connected to the second port 34 of the inhalation device 32 in valve-free manner.

In the embodiment shown, the chamber 38 comprises a preferably central outlet opening 44 to which the second port 34 is attached, preferably on a straight extension of the main direction of flow of the aerosol 14 which is preferably at least substantially straight. However, other design solutions are also possible.

The inhalation device 32 preferably comprises an outlet valve 45 via which the second port 34 is attached to the third port 35 parallel to the chamber 38 such that breathable air can flow from the second port 34 past the chamber 38 through the outlet valve 45 to the third port 35. In particular, a flow path—in this embodiment and intermediate or annular chamber—is formed between the chamber 38 or a preferably substantially cylindrical wall that forms the chamber 38, on the one hand, and the housing 39, on the other hand, said intermediate or annular chamber allowing the breathable air to flow from the second port 34 through the outlet valve 45 to the third port 35.

The outlet valve 45 preferably comprises a plurality of valve openings 46 arranged particularly in a ring around a periphery of the intermediate chamber or annular chamber, which can be closed off by a common or a plurality of separate valve elements 47, in the embodiment shown.

The outlet valve 45 is preferably in the form of a one-way or non-return valve.

The outlet valve 45 or its valve element 47 is preferably embodied to be self-closing and/or (slightly) biased into the closed position.

The valve element 42 and/or 47 is preferably configured in one piece and/or may be deformed by elastic deformation from the closed position into an open position. However, other design solutions are also possible.

The outlet valve 45 is preferably arranged concentrically with the inlet valve 40 and/or adjacent to the inlet valve and/or arranged around the inlet valve 40. However, other design solutions or arrangements are also possible.

The inlet valve 40 and/or outlet valve 45 is preferably arranged in the region of the inlet of the chamber 38 or adjacent to the connecting channel 43.

Figure 13:
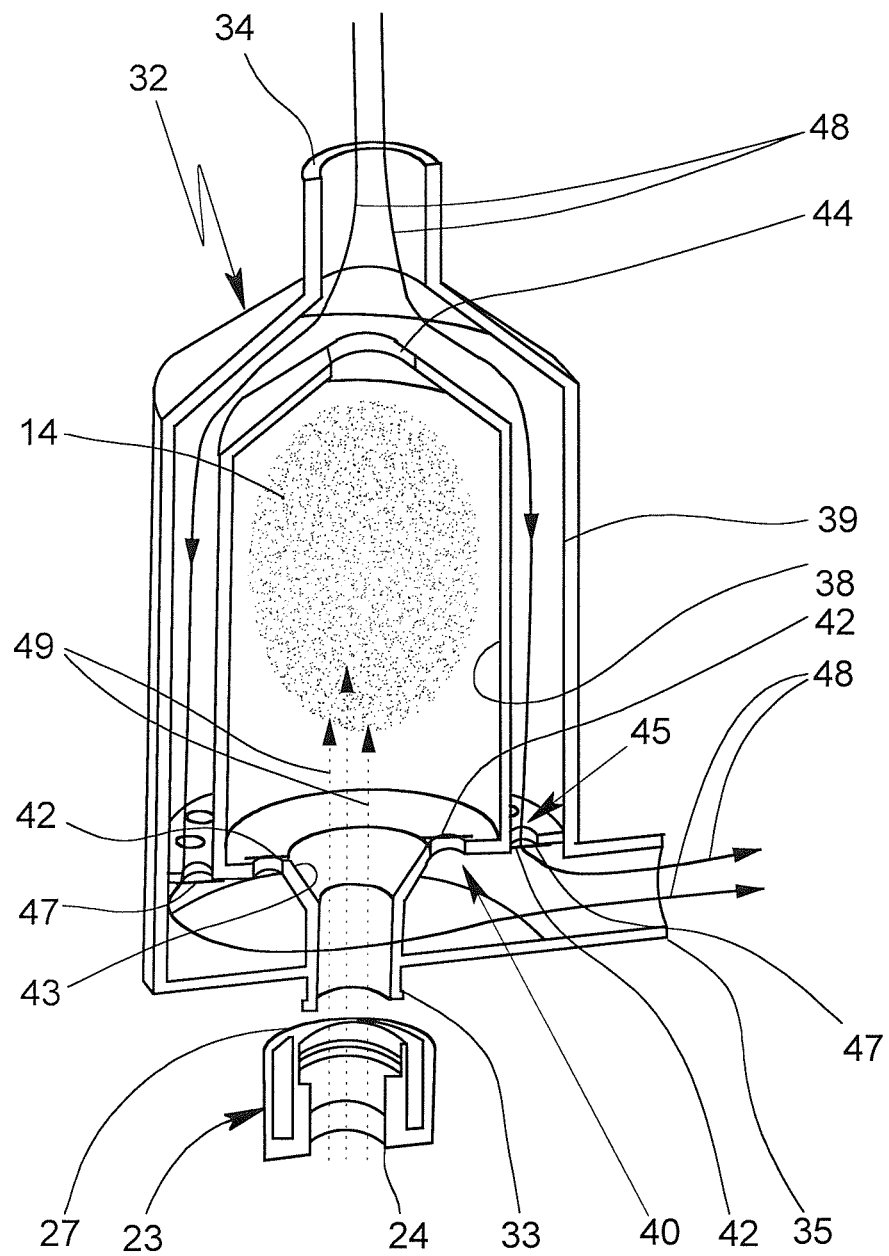
FIG. 13 is a schematic section through the inhalation device during breathing out.

FIG. 13 shows in a schematic sectional representation the air flow when breathing out. The breathed-out air 48 can flow into the inhalation device 32 through the second port 34 and from there past the chamber 38 or around the chamber 38 through the outlet valve 45, which opens automatically, to the third port 35 and from this it can flow out of the inhalation device 32, as indicated by arrows 48. This breathed-out air 48 cannot flow into the chamber 38 as the inlet valve 40 is closed in this direction or closes automatically.

FIG. 13 schematically shows, by means of dashed arrows 49, how the aerosol 14 can flow, optionally simultaneously or in parallel or independently thereof, from the nebuliser 1 (not shown) through the optional adaptor 23, the first port 33 and the connecting channel 43 into the chamber 38 where it forms an aerosol mist 14. This aerosol mist is not affected by the breathed-out air 48.

Figure 14:
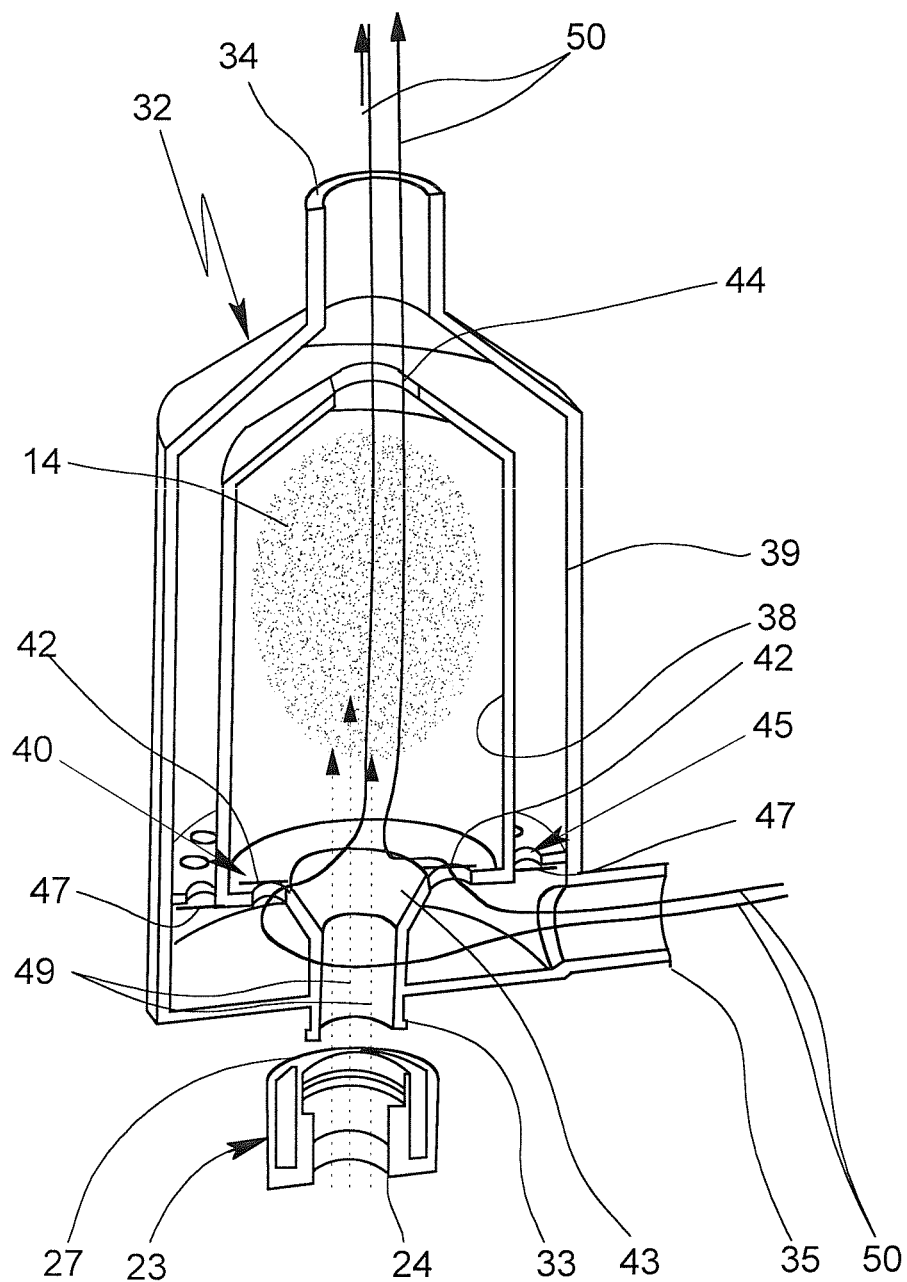

FIG. 14 shows the situation when breathing in, i.e. when breathable air flows through the third port 35 into the inhalation device 32 and is delivered through the second port 34 to the patient (not shown), particularly through a tube, face mask, other ventilation device or a mouthpiece or the like (not shown) to the patient (not shown). The thus breathed-in air is indicated by arrows 50 in FIG. 14. The breathed-in air 50 flows through the inlet valve 40 which opens automatically in this direction, into the chamber 38 on the inlet side, and flows together with the aerosol 14 which is carried along in particular by the breathed-in air 50, through the preferably constantly open outlet opening 44 of the chamber 38 and onto the second port 34, i.e. out of the inhalation device 32. The breathed-in air 50 cannot flow around the chamber 38 through the outlet valve 45 as the outlet valve 45 is closed or closes automatically in this direction.

Figure 15:
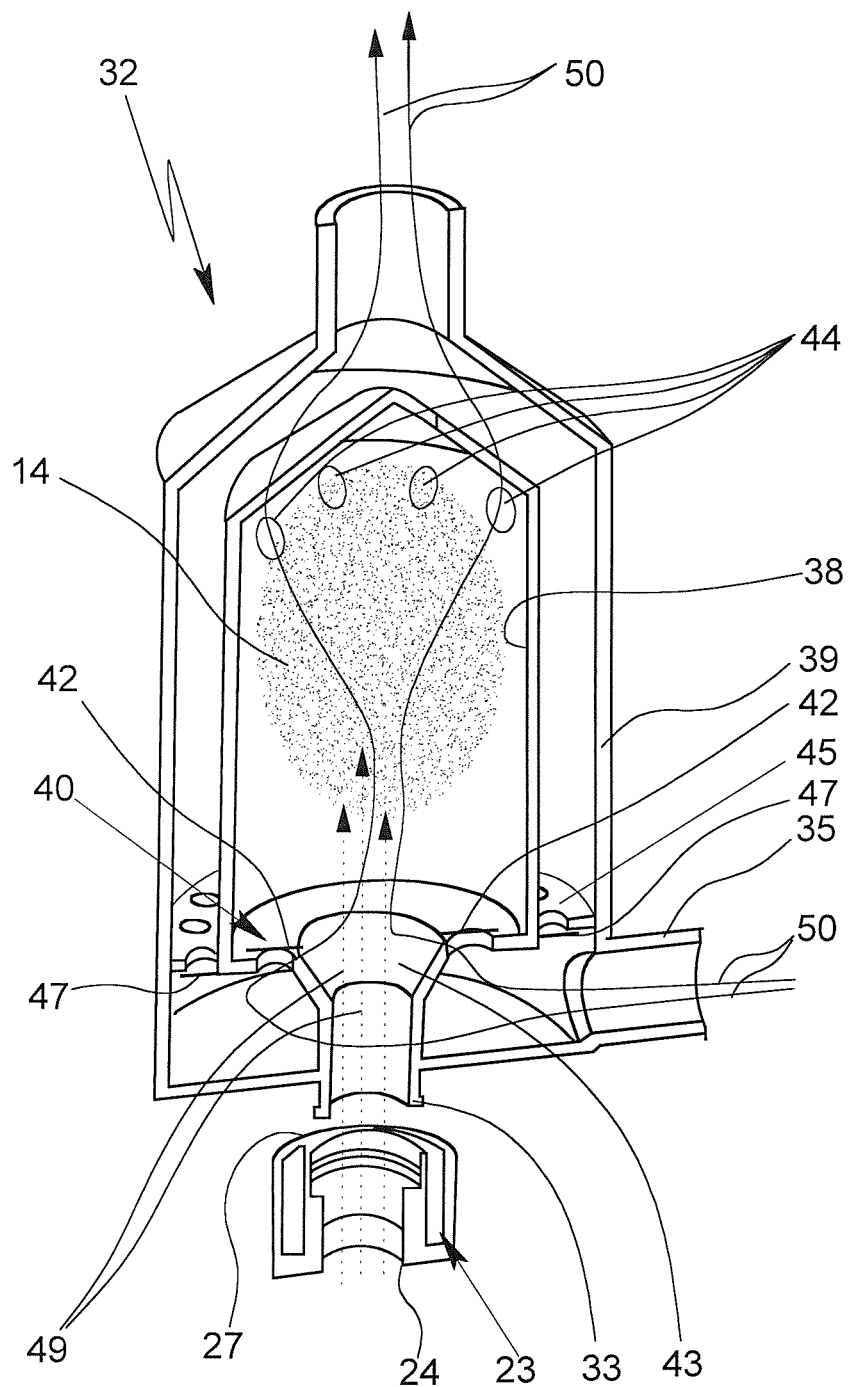

FIG. 15 shows a second embodiment of the proposed inhalation device 32, in a view corresponding to FIG. 14, during breathing in, i.e. during the supplying of breathable air to a patient (not shown). In contrast to the first embodiment the inhalation device 32 according to the second embodiment comprises a plurality of outlet openings 44 at the chamber 38 which are arranged in particular in an annular arrangement and/or concentrically with respect to the preferably central second port 34 (the second port 34 adjoins the annular arrangement of the outlet openings 44 particularly axially or downstream). Tests have shown that, surprisingly, this results in a dispensing of the aerosol 14 free from wastage while ensuring thorough mixing with the breathed-in air 50 which is supplied or sucked in.

It should be noted that the inlet valve 40 is preferably configured such that its valve element 42 opens towards the centre or towards the connecting channel 43 or the free end or free edge points towards the centre. In particular, this or another configuration ensures that breathed-in air 50 flowing into the chamber 38 flows in adjacent to the end of the connecting channel 43 in order to produce an additional Venturi effect, if required. However, other design solutions are also possible.

Generally speaking, it should be noted that the individual embodiments and alternatives and the respective features and aspects may be combined with one another in any desired manner but may also be implemented of one another.

The present invention proposes in particular a combination of the nebuliser 1 described above or some other nebuliser 1 with the adaptor 23 and the inhalation device 32. However, the adaptor 23 and the inhalation device 32 may also be used independently of one another in conjunction with the nebuliser 1 or with other nebulisers 1.

Furthermore, the present invention is directed to using the adaptor 23 and/or the inhalation device 32 with a ventilating apparatus or for ventilating a patient. However, the inhalation device 32 may also, in particular, be used for other purposes, for example as a so-called spacer. In this case the third port 35 can be omitted or it may be connected to the nebuliser 1. If necessary the breathable air or supply air can then be supplied through at least one supply air opening 15 of the nebuliser 1 or by some other method. Alternatively, the third port 35 may be used only for admitting breathed-out air 48.

To complete the disclosure of the present application and with regard to the preferred embodiment of the nebuliser 1, reference is hereby made, in precautionary manner, to the total disclosure of both WO 91/14468 A1 and also WO 97/12687 A1.

In contrast to free-standing appliances or the like, the proposed nebuliser 1 is preferably designed to be portable and in particular is a mobile hand-held device.

By virtue of its cylindrical shape and handy size of less than 9 to 15 cm long and 2 to 4 cm wide, the nebuliser 1 can be carried by the patient at all times. The nebuliser sprays a defined volume of the medicament preparation 2 by the application of high pressures through small nozzles, so as to form inhalable aerosols 14.

The nebuliser 1 operates purely mechanically, in particular. However, the nebuliser 1 may theoretically operate by any other method. In particular, the expression "conveying device" or "pressure generator" must be understood in very general terms. For example, the pressure required for the delivery and nebulisation may also be generated by propellant gas, a pump or by any other suitable method.

The nebuliser 1 is designed in particular for the brief nebulisation of the medicament preparation 2, for example for one to two breaths. However, it may also be designed or used for longer or continuous nebulisation.

Some preferred ingredients, compounds and/or formulations of the fluid or the medicament preparation 2 are listed below.

The compounds listed below may be used in the device according to the invention on their own or in combination. In the compounds mentioned below, W is a pharmacologically active substance and is selected (for example) from among the betamimetics, anticholinergics, corticosteroids, PDE4-inhibitors, LTD4-antagonists, EGFR-inhibitors, dopamine agonists, H1-antihistamines, PAF-antagonists and PI3-kinase inhibitors. Moreover, double or triple combinations of W may be combined and used in the device according to the invention. Combinations of W might be, for example:

- W denotes a betamimetic, combined with an anticholinergic, corticosteroid, PDE4-inhibitor, EGFR-inhibitor or LTD4-antagonist,
- W denotes an anticholinergic, combined with a betamimetic, corticosteroid, PDE4-inhibitor, EGFR-inhibitor or LTD4-antagonist,
- W denotes a corticosteroid, combined with a PDE4-inhibitor, EGFR-inhibitor or LTD4-antagonist
- W denotes a PDE4-inhibitor, combined with an EGFR-inhibitor or LTD4-antagonist
- W denotes an EGFR-inhibitor, combined with an LTD4-antagonist.

The compounds used as betamimetics are preferably compounds selected from among albuterol, arformoterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmefamol, salmeterol, soterenol, sulphonterol, terbutaline, tiaramide, tolubuterol, zinterol, CHF-1035, HOKU-81, KUL-1248 and

- 3-(4-{6-[2-hydroxy-2-(4-hydroxy-3-hydroxymethyl-phenyl)-ethylamino]-hexyloxy}-butyl)-benzyl-sulphonamide
- 5-[2-(5,6-diethyl-indan-2-ylamino)-1-hydroxy-ethyl]-8-hydroxy-1H-quinolin-2-one
- 4-hydroxy-7-[2-{[2-{[3-(2-phenylethoxy)propyl]sulphonyl}ethyl]-amino}ethyl]-2(3H)-benzothiazolone
- 1-(2-fluoro-4-hydroxyphenyl)-2-[4-(1-benzimidazolyl)-2-methyl-2-butylamino]ethanol
- 1[3-(4-methoxybenzyl-amino)-4-hydroxyphenyl]-2[4-(1-benzimidazolyl)-2-methyl-2-butylamino]ethanol
- 1-[2H-5-hydroxy-3-oxo-4H-1,4-benzoxazin-8-yl]-2-[3-(4-N,N-dimethylaminophenyl)-2-methyl-2-propylamino]ethanol
- 1-[2H-5-hydroxy-3-oxo-4H-1,4-benzoxazin-8-yl]-2-[3-(4-methoxyphenyl)-2-methyl-2-propylamino]ethanol
- 1-[2H-5-hydroxy-3-oxo-4H-1,4-benzoxazin-8-yl]-2-[3-(4-n-butyloxyphenyl)-2-methyl-2-propylamino]ethanol
- 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol
- 5-hydroxy-8-(1-hydroxy-2-isopropylaminobutyl)-2H-1,4-benzoxazin-3-(4H)-one
- 1-(4-amino-3-chloro-5-trifluoromethylphenyl)-2-tert.-butylamino)ethanol
- 6-hydroxy-8-{1-hydroxy-2-[2-(4-methoxy-phenyl)-1,1-dimethyl-ethylamino]-ethyl}-4H-benzo[1,4]oxazin-3-one
- 6-hydroxy-8-{1-hydroxy-2-[2-(ethyl4-phenoxy-acetate)-1,1-dimethyl-ethylamino]-ethyl}-4H-benzo[1,4]oxazin-3-one
- 6-hydroxy-8-{1-hydroxy-2-[2-(4-phenoxy-acetic acid)-1,1-dimethyl-ethylamino]-ethyl}-4H-benzo[1,4]oxazin-3-one
- 8-{2-[1,1-dimethyl-2-(2,4,6-trimethylphenyl)-ethylamino]-1-hydroxy-ethyl}-6-hydroxy-4H-benzo[1,4]oxazin-3-one
- 6-hydroxy-8-{1-hydroxy-2-[2-(4-hydroxy-phenyl)-1,1-dimethyl-ethylamino]-ethyl}-4H-benzo[1,4]oxazin-3-one
- 6-hydroxy-8-{1-hydroxy-2-[2-(4-isopropyl-phenyl)-1.1dimethyl-ethylamino]-ethyl}-4H-benzo[1,4]oxazin-3-one
- 8-{2-[2-(4-ethyl-phenyl)-1,1-dimethyl-ethylamino]-1-hydroxy-ethyl}-6-hydroxy-4H-benzo[1,4]oxazin-3-one
- 8-{2-[2-(4-ethoxy-phenyl)-1,1-dimethyl-ethylamino]-1-hydroxy-ethyl}-6-hydroxy-4H-benzo[1,4]oxazin-3-one
- 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid
- 8-{2-[2-(3.4-difluoro-phenyl)-1,1-dimethyl-ethylamino]-1-hydroxy-ethyl}-6-hydroxy-4H-benzo[1,4]oxazin-3-one
- 1-(4-ethoxy-carbonylamino-3-cyano-5-fluorophenyl)-2-(tert-butylamino)ethanol
- 2-hydroxy-5-(1-hydroxy-2-{2-[4-(2-hydroxy-2-phenyl-ethylamino)-phenyl]-ethylamino}-ethyl)-benzaldehyde
- N-[2-hydroxy-5-(1-hydroxy-2-{2-[4-(2-hydroxy-2-phenyl-ethylamino)-phenyl]-ethylamino}-ethyl)-phenyl]-formamide
- 8-hydroxy-5-(1-hydroxy-2-{2-[4-(6-methoxy-biphenyl-3-ylamino)-phenyl]-ethylamino}-ethyl)-1H-quinolin-2-one
- 8-hydroxy-5-[1-hydroxy-2-(6-phenethylamino-hexylamino)-ethyl]-1H-quinolin-2-one
- 5-[2-(2-{4-[4-(2-amino-2-methyl-propoxy)-phenylamino]-phenyl}-ethylamino)-1-hydroxy-ethyl]-8-hydroxy-1H-quinolin-2-one
- [3-(4-{6-[2-hydroxy-2-(4-hydroxy-3-hydroxymethyl-phenyl)-ethylamino]-hexyloxy}-butyl)-5-methyl-phenyl]-urea
- 4-(2-{6-[2-(2,6-dichloro-benzyloxy)-ethoxy]-hexylamino}-1-hydroxy-ethyl)-2-hydroxymethyl-phenol
- 3-(4-{6-[2-hydroxy-2-(4-hydroxy-3-hydroxymethyl-phenyl)-ethylamino]-hexyloxy}-butyl)-benzylsulphonamide
- 3-(3-{7-[2-hydroxy-2-(4-hydroxy-3-hydroxymethyl-phenyl)-ethylamino]-heptyloxy}-propyl)-benzylsulphonamide
- 4-(2-{6-[4-(3-cyclopentanesulphonyl-phenyl)-butoxy]-hexylamino}-1-hydroxy-ethyl)-2-hydroxymethyl-phenol
- N-Adamantan-2-yl-2-(3-{2-[2-hydroxy-2-(4-hydroxy-3-hydroxymethyl-phenyl)-ethylamino]-propyl}-phenyl)-acetamide optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The anticholinergics used are preferably compounds selected from among the tiotropium salts, preferably the bromide salt, oxitropium salts, preferably the bromide salt, flutropium salts, preferably the bromide salt, ipratropium salts, preferably the bromide salt, glycopyrronium salts, preferably the bromide salt, trospium salts, preferably the chloride salt, tolterodine. In the above-mentioned salts the cations are the pharmacologically active constituents. As anions the above-mentioned salts may preferably contain the chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts the chlorides, bromides, iodides and methanesulphonates are particularly preferred.

Other preferred anticholinergics are selected from among the salts of formula AC-1

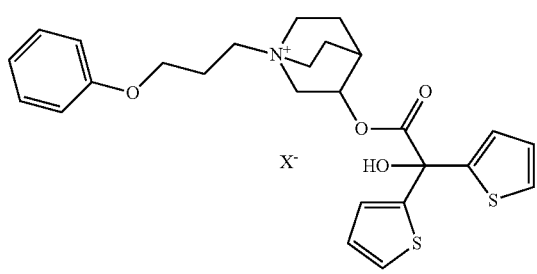

AC-1 wherein $X^-$ denotes an anion with a single negative charge, preferably an anion selected from among the fluoride, chloride, bromide, iodide, sulphate, phosphate, methanesulphonate, nitrate, maleate, acetate, citrate, fumarate, tartrate, oxalate, succinate, benzoate and p-toluenesulphonate, preferably an anion with a single negative charge, particularly preferably an anion selected from among the fluoride, chloride, bromide, methanesulphonate and p-toluenesulphonate, particularly preferably bromide, optionally in the form of the racemates, enantiomers or hydrates thereof. Of particular importance are those pharmaceutical combinations which contain the enantiomers of formula AC-1-en

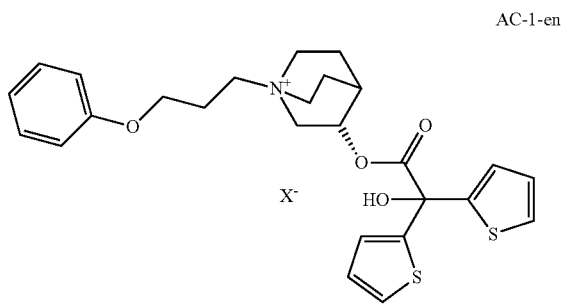

AC-1-en wherein $X^-$ may have the above-mentioned meanings. Other preferred anticholinergics are selected from the salts of formula AC-2

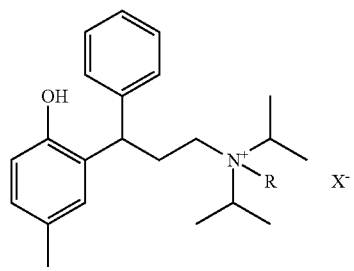

AC-2 wherein R denotes either methyl or ethyl and wherein $X^-$ may have the above-mentioned meanings. In an alternative embodiment the compound of formula AC-2 may also be present in the form of the free base AC-2-base.

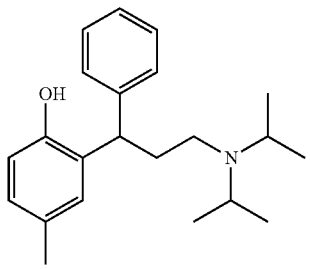

AC-2-base

Other specified compounds are:
tropenol 2,2-diphenylpropionate methobromide,
scopine 2,2-diphenylpropionate methobromide,
scopine 2-fluoro-2,2-diphenylacetate methobromide,
tropenol 2-fluoro-2,2-diphenylacetate methobromide;
tropenol 3,3',4,4'-tetrafluorobenzilate methobromide,
scopine 3,3',4,4'-tetrafluorobenzilate methobromide,
tropenol 4,4'-difluorobenzilate methobromide,
scopine 4,4'-difluorobenzilate methobromide,
tropenol 3,3'-difluorobenzilate methobromide,
scopine 3,3'-difluorobenzilate methobromide;
tropenol 9-hydroxy-fluorene-9-carboxylate methobromide;
tropenol 9-fluoro-fluorene-9-carboxylate methobromide;
scopine 9-hydroxy-fluorene-9-carboxylate methobromide;
scopine 9-fluoro-fluorene-9-carboxylate methobromide;
tropenol 9-methyl-fluorene-9-carboxylate methobromide;
scopine 9-methyl-fluorene-9-carboxylate methobromide;
cyclopropyltropine benzilate methobromide;
cyclopropyltropine 2,2-diphenylpropionate methobromide;
cyclopropyltropine 9-hydroxy-xanthene-9-carboxylate methobromide;
cyclopropyltropine 9-methyl-fluorene-9-carboxylate methobromide;
cyclopropyltropine 9-methyl-xanthene-9-carboxylate methobromide;
cyclopropyltropine 9-hydroxy-fluorene-9-carboxylate methobromide;
cyclopropyltropine methyl 4,4'-difluorobenzilate methobromide.
tropenol 9-hydroxy-xanthene-9-carboxylate methobromide;
scopine 9-hydroxy-xanthene-9-carboxylate methobromide;
tropenol 9-methyl-xanthene-9-carboxylate methobromide;
scopine 9-methyl-xanthene-9-carboxylate methobromide;
tropenol 9-ethyl-xanthene-9-carboxylate methobromide;
tropenol 9-difluoromethyl-xanthene-9-carboxylate methobromide;
scopine 9-hydroxymethyl-xanthene-9-carboxylate methobromide, The above-mentioned compounds may also be used as salts within the scope of the present invention, wherein instead of the methobromide the metho-X salts are used, wherein X may have the meanings given hereinbefore for $X^-$.

As corticosteroids it is preferable to use compounds selected from among beclomethasone, betamethasone, budesonide, butixocort, ciclesonide, deflazacort, dexamethasone, etiprednol, flunisolide, fluticasone, loteprednol, mometasone, prednisolone, prednisone, rofleponide, triamcinolone, RPR-106541, NS-126, ST-26 and (S)-fluoromethyl6,9-difluoro-17-[(2-furanylcarbonyl)oxy]-11-hydroxy-16-methyl-3-oxo-androsta-1,4-diene-17-carbothionate (S)-(2-oxo-tetrahydro-furan-3S-yl)6,9-difluoro-11-hydroxy-16-methyl-3-oxo-17-propionyloxy-androsta-1,4-diene-17-carbothionate, cyanomethyl6α,9α-difluoro-11 β-hydroxy-16α-methyl-3-oxo-17α-(2,2,3,3-tertamethylcyclopropylcarbonyl)oxy-androsta-1,4-diene-17β-carboxylate optionally in the form of the racemates, enantiomers or diastereomers thereof and optionally in the form of the salts and derivatives thereof, the solvates and/or hydrates thereof. Any reference to steroids includes a reference to any salts or derivatives, hydrates or solvates thereof which may exist. Examples of possible salts and derivatives of the steroids may be: alkali metal salts, such as for example sodium or potassium salts, sulphobenzoates, phosphates, isonicotinates, acetates, dichloroacetates, propionates, dihydrogen phosphates, palmitates, pivalates or furoates.

PDE4-inhibitors which may be used are preferably compounds selected from among enprofyllin, theophyllin, roflumilast, ariflo (cilomilast), tofimilast, pumafentrin, lirimilast, arofyllin, atizoram, D-4418, Bay-198004, BY343, CP-325.366, D-4396 (Sch-351591), AWD-12-281 (GW-842470), NCS-613, CDP-840, D-4418, PD-168787, T-440, T-2585, V-11294A, CI-1018, CDC-801, CDC-3052, D-22888, YM-58997, Z-15370 and N-(3,5-dichloro-1-oxo-pyridin-4-yl)-4-difluoromethoxy-3-cyclopropylmethoxybenzamide (−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide (R)-(+)-1-(4-bromobenzyl)-4-[(3-cyclopentyloxy)-4-methoxyphenyl]-2-pyrrolidone 3-(cyclopentyloxy-4-methoxyphenyl)-1-(4-N'-[N-2-cyano-S-methyl-isothioureido]benzyl)-2-pyrrolidone cis[4-cyano-4-(3-cyclopentyloxy-4-methoxyphenyl)cyclohexane-1-carboxylic acid]

2-carbomethoxy-4-cyano-4-(3-cyclopropylmethoxy-4-difluoromethoxyphenyl)cyclohexan-1-one cis[4-cyano-4-(3-cyclopropylmethoxy-4-difluoromethoxyphenyl)cyclohexan-1-ol]

(R)-(+)-ethyl[4-(3-cyclopentyloxy-4-methoxyphenyl)pyrrolidin-2-ylidene]acetate (S)-(−)-ethyl[4-(3-cyclopentyloxy-4-methoxyphenyl)pyrrolidin-2-ylidene]acetate 9-cyclopentyl-5,6-dihydro-7-ethyl-3-(2-thienyl)-9H-pyrazolo[3,4-c]-1,2,4-triazolo[4,3-a]pyridine 9-cyclopentyl-5,6-dihydro-7-ethyl-3-(tert-butyl)-9H-pyrazolo[3,4-c]-1,2,4-triazolo[4,3-a]pyridine optionally in the form of the racemates, enantiomers or diastereomers thereof and optionally in the form of the pharmacologically acceptable acid addition salts thereof, the solvates and/or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The LTD4-antagonists used are preferably compounds selected from among montelukast, pranlukast, zafirlukast, MCC-847 (ZD-3523), MN-001, MEN-91507 (LM-1507), VUF-5078, VUF-K-8707, L-733321 and 1-(((R)-(3-(2-(6,7-difluoro-2-quinolinyl)ethenyl)phenyl)-3-(2-(2-hydroxy-2-propyl)phenyl)thio)methylcyclopropane-acetic acid, 1-(((1(R)-3-(3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropaneacetic acid

[2-[[2-(4-tert-butyl-2-thiazolyl)-5-benzofuranyl]oxymethyl]phenyl]acetic acid optionally in the form of the racemates, enantiomers or diastereomers thereof and optionally in the form of the pharmacologically acceptable acid addition salts, solvates and/or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate. By salts or derivatives which the LTD4-antagonists may optionally be capable of forming are meant, for example: alkali metal salts, such as for example sodium or potassium salts, alkaline earth metal salts, sulphobenzoates, phosphates, isonicotinates, acetates, propionates, dihydrogen phosphates, palmitates, pivalates or furoates.

EGFR-inhibitors which may be used are preferably compounds selected from among cetuximab, trastuzumab, ABX-EGF, Mab ICR-62 and 4-[(3-chloro-4-fluorophenyl)amino]-6-{[4-(morpholin-4-yl)-1-oxo-2-buten-1-yl]amino}-7-cyclopropylmethoxy-quinazoline 4-[(3-chloro-4-fluorophenyl)amino]-6-{[4-(N,N-diethyl-amino)-1-oxo-2-buten-1-yl]amino}-7-cyclopropyl-methoxy-quinazoline 4-[(3-chloro-4-fluorophenyl)amino]-6-{[4-(N,N-dimethyl-amino)-1-oxo-2-buten-1-yl]amino}-7-cyclopropyl-methoxy-quinazoline 4-[(R)-(1-phenyl-ethyl)amino]-6-{[4-(morpholin-4-yl)-1-oxo-2-buten-1-yl]amino}-7-cyclopentyloxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline 4-[(3-chloro-4-fluoro-phenyl)amino]-6-[2-((S)-6-methyl-2-oxo-morpholin-4-yl)-ethoxy]-7-methoxy-quinazoline 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethyl-amino)-1-oxo-2-buten-1-yl]amino}-7-cyclopentyloxy-quinazoline 4-[(R)-(1-phenyl-ethyl)amino]-6-{[4-(N,N-to-(2-methoxy-ethyl)-amino)-1-oxo-2-buten-1-yl]amino}-7-cyclopropylmethoxy-quinazoline 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethyl-amino)-1-oxo-2-buten-1-yl]amino}-7-((R)-tetrahydro-furan-3-yloxy)-quinazoline 4-[(3-chloro-4-fluorophenyl)amino]-6-{[4-(N,N-dimethyl-amino)-1-oxo-2-buten-1-yl]amino}-7-((S)-tetrahydro-furan-3-yloxy)-quinazoline 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline 4-[(3-chloro-4-fluorophenyl)amino]-6-{[4-(N-cyclopropyl-N-methyl-amino)-1-oxo-2-buten-1-yl]amino}-7-cyclopentyloxy-quinazoline 4-[(3-chloro-4-fluorophenyl)amino]-6-{[4-(N,N-dimethyl-amino)-1-oxo-2-buten-1-yl]amino}-7-[(R)-(tetrahydro-furan-2-yl)methoxy]-quinazoline 4-[(3-chloro-4-fluorophenyl)amino]-6-{[4-(N,N-dimethyl-amino)-1-oxo-2-buten-1-yl]amino}-7-[(S)-(tetrahydro-furan-2-yl)methoxy]-quinazoline 4-[(3-ethynyl-phenyl)amino]-6.7-to-(2-methoxy-ethoxy)-quinazoline 4-[(3-chloro-4-fluorophenyl)amino]-7-[3-(morpholin-4-yl)-propyloxy]-6-[(vinyl-carbonyl)amino]-quinazoline 4-[(R)-(1-phenyl-ethyl)amino]-6-(4-hydroxy-phenyl)-7H-pyrrolo[2,3-d]pyrimidine 3-cyano-4-[(3-chloro-4-fluorophenyl)amino]-6-{[4-(N,N-dimethylamino)-1-oxo-2-buten-1-yl]amino}-7-ethoxy-quinoline 4-{[3-chloro-4-(3-fluoro-benzyloxy)-phenyl]amino}-6-(5-{[(2-methanesulphonyl-ethyl)amino]methyl}-furan-2-yl) quinazoline 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline 4-[(3-chloro-4-fluorophenyl)amino]-6-({4-[N,N-to-(2-methoxy-ethyl)-amino]-1-oxo-2-buten-1-yl}amino)-7-[(tetrahydrofuran-2-yl)methoxy]-quinazoline 4-[(3-ethynyl-phenyl)amino]-6-{[4-(5.5-dimethyl-2-oxo-morpholin-4-yl)-1-oxo-2-buten-1-yl]amino}-quinazoline 4-[(3-chloro-4-fluoro-phenyl)amino]-6-[2-(2,2-dimethyl-6-oxo-morpholin-4-yl)-ethoxy]-7-methoxy-quinazoline 4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline 4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline 4-[(3-chloro-4-fluoro-phenyl)amino]-6-{2-[4-(2-oxo-morpholin-4-yl)-piperidin-1-yl]-ethoxy}-7-methoxy-quinazoline 4-[(3-chloro-4-fluoro-phenyl)amino]-6-[1-(tert.-butyloxy-carbonyl)-piperidin-4-yloxy]-7-methoxy-quinazoline 4-[(3-chloro-4-fluoro-phenyl)amino]-6-(trans-4-amino-cyclohexan-1-yloxy)-7-methoxy-quinazoline 4-[(3-chloro-4-fluoro-phenyl)amino]-6-(trans-4-methane-sulphonylamino-cyclohexan-1-yloxy)-7-methoxy-quinazoline 4-[(3-chloro-4-fluoro-phenyl)amino]-6-(tetrahydropyran-3-yloxy)-7-methoxy-quinazoline 4-[(3-chloro-4-fluoro-phenyl)amino]-6-(1-methyl-piperidin-4-yloxy)-7-methoxy-quinazoline 4-[(3-chloro-4-fluoro-phenyl)amino]-6-{1-[(morpholin-4-yl)carbonyl]-piperidin-4-yloxy}-7-methoxy-quinazoline 4-[(3-chloro-4-fluoro-phenyl)amino]-6-{1-[(methoxym-ethyl)carbonyl]-piperidin-4-yloxy}-7-methoxy-quinazoline 4-[(3-chloro-4-fluoro-phenyl)amino]-6-(piperidin-3-yloxy)-7-methoxy-quinazoline 4-[(3-chloro-4-fluoro-phenyl)amino]-6-[1-(2-acetylamino-ethyl)-piperidin-4-yloxy]-7-methoxy-quinazoline 4-[(3-chloro-4-fluoro-phenyl)amino]-6-(tetrahydropyran-4-yloxy)-7-ethoxy-quinazoline 4-[(3-chloro-4-fluoro-phenyl)amino]-6-((S)-tetrahydro-furan-3-yloxy)-7-hydroxy-quinazoline 4-[(3-chloro-4-fluoro-phenyl)amino]-6-(tetrahydropyran-4-yloxy)-7-(2-methoxy-ethoxy)-quinazoline 4-[(3-chloro-4-fluoro-phenyl)amino]-6-{trans-4-[(dimeth-ylamino)sulphonylamino-cyclohexan-1-yloxy}-7-methoxy-quinazoline 4-[(3-chloro-4-fluoro-phenyl)amino]-6-{trans-4-[(morpho-lin-4-yl)carbonylamino]-cyclohexan-1-yloxy}-7-methoxy-quinazoline 4-[(3-chloro-4-fluoro-phenyl)amino]-6-{trans-4-[(morpho-lin-4-yl)sulphonylamino]-cyclohexan-1-yloxy}-7-methoxy-quinazoline 4-[(3-chloro-4-fluoro-phenyl)amino]-6-(tetrahydropyran-4-yloxy)-7-(2-acetylamino-ethoxy)-quinazoline 4-[(3-chloro-4-fluoro-phenyl)amino]-6-(tetrahydropyran-4-yloxy)-7-(2-methanesulphonylamino-ethoxy)-quinazoline 4-[(3-chloro-4-fluoro-phenyl)amino]-6-{1-[(piperidin-1-yl)carbonyl]-piperidin-4-yloxy}-7-methoxy-quinazoline 4-[(3-chloro-4-fluoro-phenyl)amino]-6-(1-aminocarbonyl-methyl-piperidin-4-yloxy)-7-methoxy-quinazoline 4-[(3-chloro-4-fluoro-phenyl)amino]-6-(cis-4-{N-[(tetrahy-dropyran-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(mor-pholin-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(mor-pholin-4-yl)sulphonyl]-N-methyl-amino}-cyclohexan-1-yloxy)-7-methoxy-quinazoline 4-[(3-chloro-4-fluoro-phenyl)amino]-6-(trans-4-ethanesul-phonylamino-cyclohexan-1-yloxy)-7-methoxy-quinazoline 4-[(3-chloro-4-fluoro-phenyl)amino]-6-(1-methanesulpho-nyl-piperidin-4-yloxy)-7-ethoxy-quinazoline 4-[(3-chloro-4-fluoro-phenyl)amino]-6-(1-methanesulpho-nyl-piperidin-4-yloxy)-7-(2-methoxy-ethoxy)-quinazo-line 4-[(3-chloro-4-fluoro-phenyl)amino]-6-[1-(2-methoxy-acetyl)-piperidin-4-yloxy]-7-(2-methoxy-ethoxy)-quinazoline 4-[(3-chloro-4-fluoro-phenyl)amino]-6-(cis-4-acetylamino-cyclohexan-1-yloxy)-7-methoxy-quinazoline 4-[(3-ethynyl-phenyl)amino]-6-[1-(tert.-butyloxycarbonyl)-piperidin-4-yloxy]-7-methoxy-quinazoline 4-[(3-ethynyl-phenyl)amino]-6-(tetrahydropyran-4-yloxy]-7-methoxy-quinazoline 4-[(3-chloro-4-fluoro-phenyl)amino]-6-(cis-4-{N-[(piperi-din-1-yl)carbonyl]-N-methyl-amino}-cyclohexan-1-yloxy)-7-methoxy-quinazoline 4-[(3-chloro-4-fluoro-phenyl)amino]-6-(cis-4-{N-[(4-methyl-piperazin-1-yl)carbonyl]-N-methyl-amino}-cy-clohexan-1-yloxy)-7-methoxy-quinazoline 4-[(3-chloro-4-fluoro-phenyl)amino]-6-{cis-4-[(morpholin-4-yl)carbonylamino]-cyclohexan-1-yloxy}-7-methoxy-quinazoline 4-[(3-chloro-4-fluoro-phenyl)amino]-6-{1-[2-(2-oxopyrrolidin-1-yl)ethyl]-piperidin-4-yloxy}-7-methoxy-quinazoline 4-[(3-chloro-4-fluoro-phenyl)amino]-6-{1-[(morpholin-4-yl)carbonyl]-piperidin-4-yloxy}-7-(2-methoxy-ethoxy)-quinazoline 4-[(3-ethynyl-phenyl)amino]-6-(1-acetyl-piperidin-4-yloxy)-7-methoxy-quinazoline 4-[(3-ethynyl-phenyl)amino]-6-(1-methyl-piperidin-4-yloxy)-7-methoxy-quinazoline 4-[(3-ethynyl-phenyl)amino]-6-(1-methanesulphonyl-piperidin-4-yloxy)-7-methoxy-quinazoline 4-[(3-chloro-4-fluoro-phenyl)amino]-6-(1-methyl-piperidin-4-yloxy)-7(2-methoxy-ethoxy)-quinazoline 4-[(3-chloro-4-fluoro-phenyl)amino]-6-(1-isopropyloxycarbonyl-piperidin-4-yloxy)-7-methoxy-quinazoline 4-[(3-chloro-4-fluoro-phenyl)amino]-6-(cis-4-methyl-amino-cyclohexan-1-yloxy)-7-methoxy-quinazoline 4-[(3-chloro-4-fluoro-phenyl)amino]-6-{cis-4-[N-(2-methoxy-acetyl)-N-methyl-amino]-cyclohexan-1-yloxy}-7-methoxy-quinazoline 4-[(3-ethynyl-phenyl)amino]-6-(piperidin-4-yloxy)-7-methoxy-quinazoline 4-[(3-ethynyl-phenyl)amino]-6-[1-(2-methoxy-acetyl)-piperidin-4-yloxy]-7-methoxy-quinazoline 4-[(3-ethynyl-phenyl)amino]-6-{1-[(morpholin-4-yl)carbonyl]-piperidin-4-yloxy}-7-methoxy-quinazoline 4-[(3-chloro-4-fluoro-phenyl)amino]-6-{1-[(cis-2,6-dimethyl-morpholin-4-yl)carbonyl]-piperidin-4-yloxy}-7-methoxy-quinazoline 4-[(3-chloro-4-fluoro-phenyl)amino]-6-{1-[(2-methyl-morpholin-4-yl)carbonyl]-piperidin-4-yloxy}-7-methoxy-quinazoline 4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline 4-[(3-chloro-4-fluoro-phenyl)amino]-6-{1-[(N-methyl-N-2-methoxyethyl-amino)carbonyl]-piperidin-4-yloxy}-7-methoxy-quinazoline 4-[(3-chloro-4-fluoro-phenyl)amino]-6-(1-ethyl-piperidin-4-yloxy)-7-methoxy-quinazoline 4-[(3-chloro-4-fluoro-phenyl)amino]-6-{1-[(2-methoxyethyl)carbonyl]-piperidin-4-yloxy}-7-methoxy-quinazoline 4-[(3-chloro-4-fluoro-phenyl)amino]-6-{1-[(3-methoxypropyl-amino)-carbonyl]-piperidin-4-yloxy}-7-methoxy-quinazoline 4-[(3-chloro-4-fluoro-phenyl)amino]-6-[cis-4-(N-methanesulphonyl-N-methyl-amino)-cyclohexan-1-yloxy]-7-methoxy-quinazoline 4-[(3-chloro-4-fluoro-phenyl)amino]-6-[cis-4-(N-acetyl-N-methyl-amino)-cyclohexan-1-yloxy]-7-methoxy-quinazoline 4-[(3-chloro-4-fluoro-phenyl)amino]-6-(trans-4-methyl-amino-cyclohexan-1-yloxy)-7-methoxy-quinazoline 4-[(3-chloro-4-fluoro-phenyl)amino]-6-[trans-4-(N-methanesulphonyl-N-methyl-amino)-cyclohexan-1-yloxy]-7-methoxy-quinazoline 4-[(3-chloro-4-fluoro-phenyl)amino]-6-(trans-4-dimethyl-amino-cyclohexan-1-yloxy)-7-methoxy-quinazoline 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline 4-[(3-chloro-4-fluoro-phenyl)amino]-6-(1-methanesulphonyl-piperidin-4-yloxy)-7-methoxy-quinazoline 4-[(3-chloro-4-fluoro-phenyl)amino]-6-(1-cyano-piperidin-4-yloxy)-7-methoxy-quinazoline optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The dopamine agonists used are preferably compounds selected from among bromocriptin, cabergoline, alpha-dihydroergocryptine, lisuride, pergolide, pramipexol, roxindol, ropinirol, talipexol, tergurid and viozan, optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate.

H1-Antihistamines which may be used are preferably compounds selected from among epinastine, cetirizine, azelastine, fexofenadine, levocabastine, loratadine, mizolastine, ketotifen, emedastine, dimetindene, clemastine, bamipine, cexchlorpheniramine, pheniramine, doxylamine, chlorophenoxamine, dimenhydrinate, diphenhydramine, promethazine, ebastine, desloratidine and meclozine, optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

In addition, inhalable macromolecules as disclosed in EP 1 003 478 A1 or CA 2297174 A1 may also be used.

In addition, the compound may be selected from among the ergot alkaloid derivatives, the triptans, the CGRP-inhibitors, the phosphodiesterase-V inhibitors, optionally in the form of the racemates, enantiomers or diastereomers thereof, optionally in the form of the pharmacologically acceptable acid addition salts, the solvates and/or hydrates thereof.

Examples of ergot alkaloid derivatives are dihydroergotamine and ergotamine.

| List of reference numerals | |
|---|---|
| 1 | nebuliser |
| 2 | medicament preparation |
| 3 | container |
| 4 | bag |
| 5 | pressure generator |

-continued

List of reference numerals

| | |
|---|---|
| 6 | holder |
| 7 | drive spring |
| 8 | locking element |
| 9 | conveying tube |
| 10 | non-return valve |
| 11 | pressure chamber |
| 12 | expulsion nozzle |
| 13 | mouthpiece |
| 14 | aerosol |
| 15 | supply air opening |
| 16 | first housing part (upper part) |
| 17 | inner part |
| 17a | upper part of the inner part |
| 17b | lower part of the inner part |
| 18 | second housing part (lower part) |
| 19 | retaining element |
| 20 | spring (in the lower housing part) |
| 21 | container base |
| 22 | piercing element |
| 23 | adapter |
| 24 | first connection (adapter) |
| 25 | connecting portion |
| 26 | connector |
| 27 | second connection (adapter) |
| 28 | third connection (adapter) |
| 29 | tube |
| 30 | annular channel |
| 31 | locking valve |
| 32 | inhalation device |
| 33 | first port (inhalation device) |
| 34 | second port (inhalation device) |
| 35 | third port (inhalation device) |
| 36 | valve element |
| 37 | projection |
| 38 | chamber |
| 39 | housing |
| 40 | inlet valve |
| 41 | inlet opening |
| 42 | valve element |
| 43 | connecting channel |
| 44 | outlet opening |
| 45 | outlet valve |
| 46 | valve opening |
| 47 | valve element |
| 48 | breathed out air |
| 49 | aerosol flow |
| 50 | breathed in air |

I claim:

1. An inhalation device (32), comprising:
a chamber (38) for intermediate storage of an aerosol (14),
a first connection (33) for a nebuliser (1) that produces the aerosol (14),
a second connection (34) on a patient side for delivering the aerosol (14), and
a third connection (35) for breathable air,
wherein:
the chamber (38) is fluidically connected in a valve-free manner on an inlet side to the first connection (33) when the nebuliser (1) is attached,
the chamber (38) is connected to the third connection (35) in parallel on the inlet side via an inlet valve (40) so that the breathable air from the third connection(35) flows into the chamber (38), and
the second connection (34) is connected to the third connection (35) via an outlet valve (45) parallel to the chamber (38), so that the breathable air flows from the second connection (34) past the chamber (38) through the outlet valve (45) to the third connection (35).

2. The inhalation device according to claim 1, wherein the chamber (38) comprises on the outlet side a plurality of outlet openings (44) arranged at least substantially in an annular configuration.

3. The inhalation device according to claim 1, wherein the chamber (38) is fluidically connected to the second connection (34) on an outlet side in valve-free manner.

4. The inhalation device according to claim 1, wherein the inlet valve (40) is a one-way or non-return valve.

5. The inhalation device according to claim 1, wherein the outlet valve (45) is a one-way or non-return valve.

6. The inhalation device according to claim 1, wherein the inhalation device (32) comprises an intermediate or annular chamber which allows the breathable air to flow from the second connection (34) through the outlet valve (45) parallel to the chamber (38) to the third connection (35), and the intermediate or annular chamber is formed between the chamber (38) or a wall that forms the chamber (38), on the one hand, and a housing (39) of the inhalation device (32), on the other hand.

7. The inhalation device according to claim 1, wherein the outlet valve (45) comprises a plurality of valve openings (46).

8. The inhalation device according to claim 7, wherein the plurality of valve openings (46) are arranged in a ring around a periphery of the intermediate chamber or annular chamber, wherein the plurality of valve openings (46) is closed off by one or more separate valve elements (47).

9. The inhalation device according to claim 1, wherein the second connection (34) is embodied as a mouthpiece (13) or for connection of a tube (29).

10. The inhalation device according to claim 1, wherein the third connection (35) is configured for connection to a ventilator.

11. The inhalation device according to claim 1, wherein the first connection (33) of the inhalation device (32) is connected or connectable to an adapter (23) having a first connection (24) for connection in a substantially leak-tight manner to a projection (37) that holds or surrounds an expulsion nozzle (12) of the nebuliser (1).

12. The inhalation device according to claim 11, wherein the adapter (23) comprises a locking valve (31) which necessarily opens when the adapter (23) is connected to the nebuliser (1) and closes when the adapter (23) is separated from the nebuliser (1).

13. A nebuliser having an inhalation device (32) according to claim 1.

14. An inhalation device (32), comprising:
a chamber (38) for intermediate storage of an aerosol (14),
a first connection (33) for a nebuliser (1) that produces the aerosol (14),
a second connection (34) on a patient side for delivering the aerosol (14), and
a third connection (35) for breathable air,
wherein:
the chamber (38) is fluidically connected in a valve-free manner on an inlet side to the first connection (33) when the nebuliser (1) is attached,
the chamber (38) is connected to the third connection (35) in parallel on the inlet side via an inlet valve (40) so that the breathable air from the third connection (35) flows into the chamber (38), and
the chamber (38) comprises on the outlet side a plurality of outlet openings (44) arranged at least substantially in an annular configuration.

* * * * *